United States Patent
Shi et al.

(10) Patent No.: US 9,561,365 B2
(45) Date of Patent: *Feb. 7, 2017

(54) SAMPLE AND HOLD CIRCUITRY FOR MONITORING VOLTAGES IN AN IMPLANTABLE NEUROSTIMULATOR

(71) Applicant: Boston Scientific Neuromodulation Corporation, Valencia, CA (US)

(72) Inventors: Jess W. Shi, Northridge, CA (US); Emanuel Feldman, Simi Valley, CA (US); Jordi Parramon, Valencia, CA (US)

(73) Assignee: Boston Scientific Neuromodulation Corporation, Valencia, CA (US)

(*) Notice: Subject to any disclaimer, the term of this patent is extended or adjusted under 35 U.S.C. 154(b) by 36 days.

This patent is subject to a terminal disclaimer.

(21) Appl. No.: 14/747,380

(22) Filed: Jun. 23, 2015

(65) Prior Publication Data

US 2015/0290456 A1    Oct. 15, 2015

Related U.S. Application Data

(63) Continuation of application No. 13/237,172, filed on Sep. 20, 2011, now Pat. No. 9,061,140.

(Continued)

(51) Int. Cl.
*G01R 27/08*    (2006.01)
*A61N 1/39*    (2006.01)
(Continued)

(52) U.S. Cl.
CPC .............. *A61N 1/08* (2013.01); *A61N 1/025* (2013.01); *A61N 1/36125* (2013.01);
(Continued)

(58) Field of Classification Search
CPC .... A61N 1/08; A61N 1/36185; A61M 1/1068; G01R 35/005; G01R 33/0082; H01L 51/0052
(Continued)

(56) References Cited

U.S. PATENT DOCUMENTS 5,603,726 A    2/1997   Schulman et al.
5,674,264 A    10/1997  Carter et al.
(Continued)

FOREIGN PATENT DOCUMENTS

WO        96/33651       10/1996
WO      2005/061044       7/2005
(Continued)

*Primary Examiner* — Melissa Koval
*Assistant Examiner* — Trung Nguyen
(74) *Attorney, Agent, or Firm* — Lewis, Reese & Nesmith, PLLC

(57) ABSTRACT

Sample and hold circuitry for monitoring electrodes and other voltages in an implantable neurostimulator is disclosed. The sample and hold circuitry in one embodiment contains multiplexers to selected appropriate voltages and to pass them to two storage capacitors during two different measurement phases. The capacitors are in a later stage serially connected to add the two voltages stored on the capacitors, and voltages present at the top and bottom of the serial connection are then input to a differential amplifier to compute their difference. The sample and hold circuitry is particularly useful in calculating the resistance between two electrodes, and is further particularly useful when resistance is measured using a biphasic pulse. The sample and hold circuitry is flexible, and can be used to measure other voltages of interest during biphasic or monophasic pulsing.

22 Claims, 24 Drawing Sheets

Related U.S. Application Data

(60) Provisional application No. 61/392,600, filed on Oct. 13, 2010.

(51) Int. Cl.
  *A61N 1/08* (2006.01)
  *A61N 1/02* (2006.01)
  *A61N 1/36* (2006.01)
  *A61N 1/378* (2006.01)
  *A61B 5/04* (2006.01)

(52) U.S. Cl.
  CPC .......... *A61N 1/378* (2013.01); *A61B 5/04001* (2013.01); *A61N 1/3937* (2013.01)

(58) Field of Classification Search
  USPC .............. 607/4, 5, 9, 55, 56, 57, 74, 34, 66, 607/119–123; 324/600, 691–693, 324/702–710, 676, 76.11, 76.77, 323, 324/360, 120
  See application file for complete search history.

(56) References Cited

U.S. PATENT DOCUMENTS

| | | |
|---|---|---|
| 5,694,943 A | 12/1997 | Brewer et al. |
| 5,876,425 A | 3/1999 | Gord et al. |
| 5,941,906 A | 8/1999 | Barreras, Sr. et al. |
| 6,516,227 B1 | 2/2003 | Meadows et al. |
| 6,525,986 B2 | 2/2003 | Prutchi et al. |
| 6,754,533 B1 | 6/2004 | Helfinstine et al. |
| 7,444,181 B2 | 10/2008 | Shi et al. |
| 7,805,189 B2 | 9/2010 | Stein et al. |
| 8,738,154 B2 * | 5/2014 | Zdeblick ................ A61N 1/025 607/117 |
| 8,823,382 B2 * | 9/2014 | Rondoni ............... A61N 1/3708 320/134 |
| 2005/0251004 A1 | 11/2005 | Istvan et al. |
| 2010/0256712 A1 | 10/2010 | Varrichio et al. |

FOREIGN PATENT DOCUMENTS

| | | |
|---|---|---|
| WO | 2006/029090 | 3/2006 |
| WO | 2007/075974 | 7/2007 |

\* cited by examiner

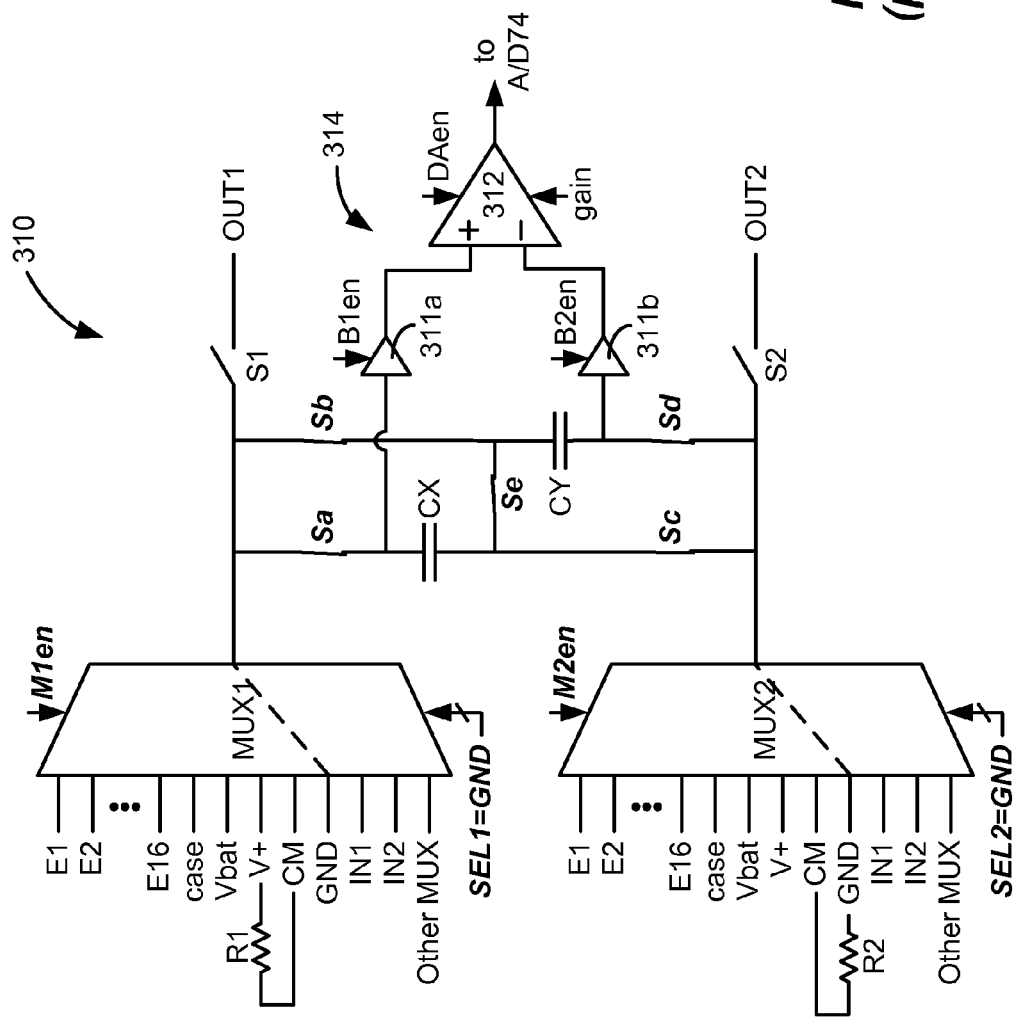
*Figure 6A (pre-stage)*

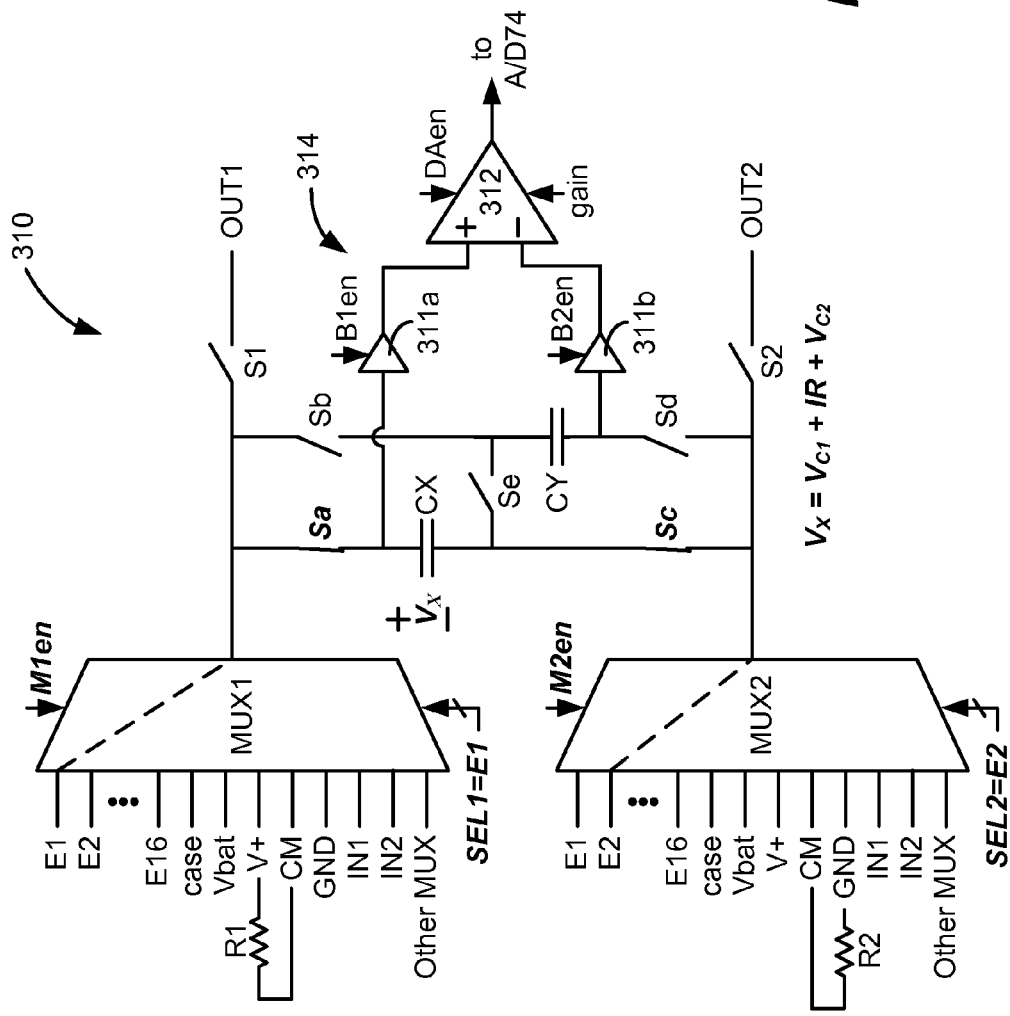
*Figure 6B (stage 1)*

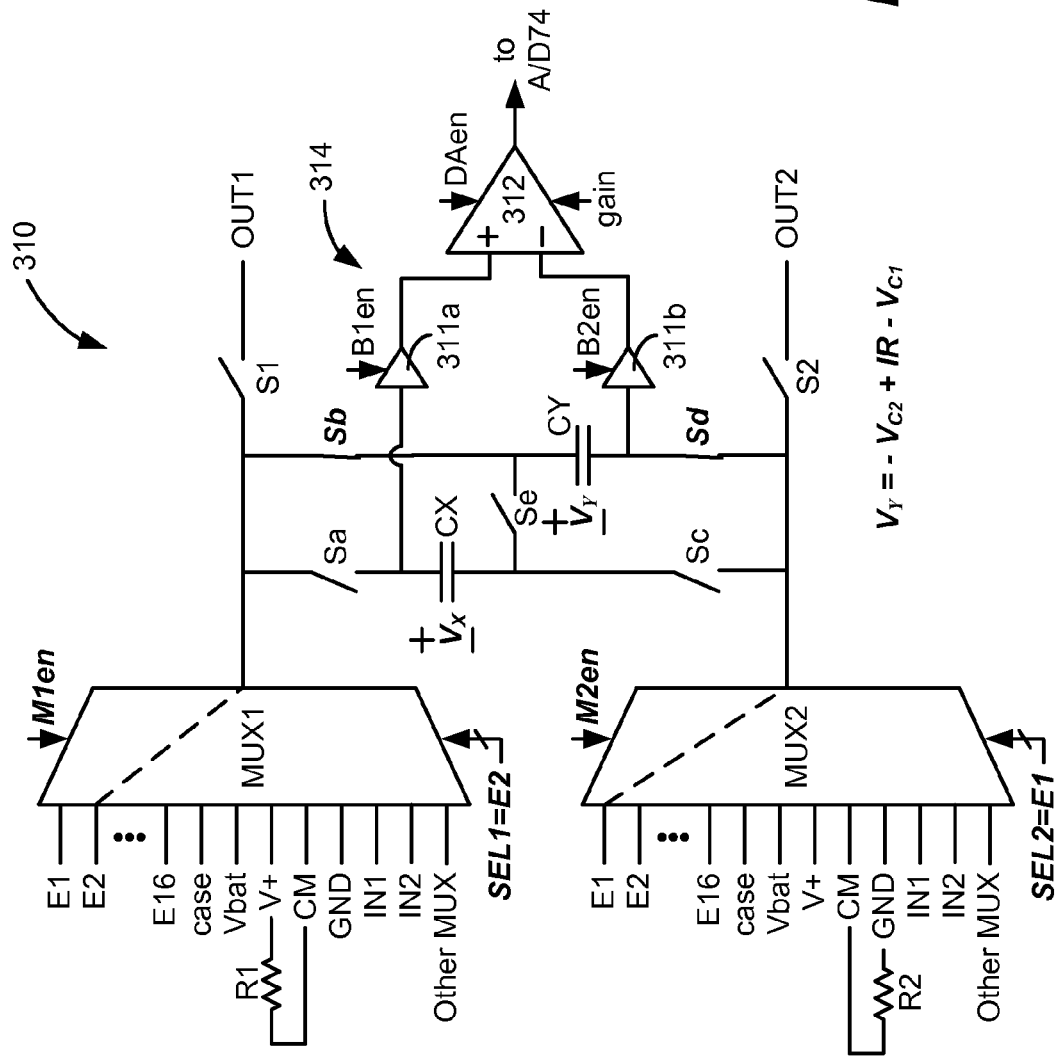
Figure 6C (stage 2)

(stage 3)

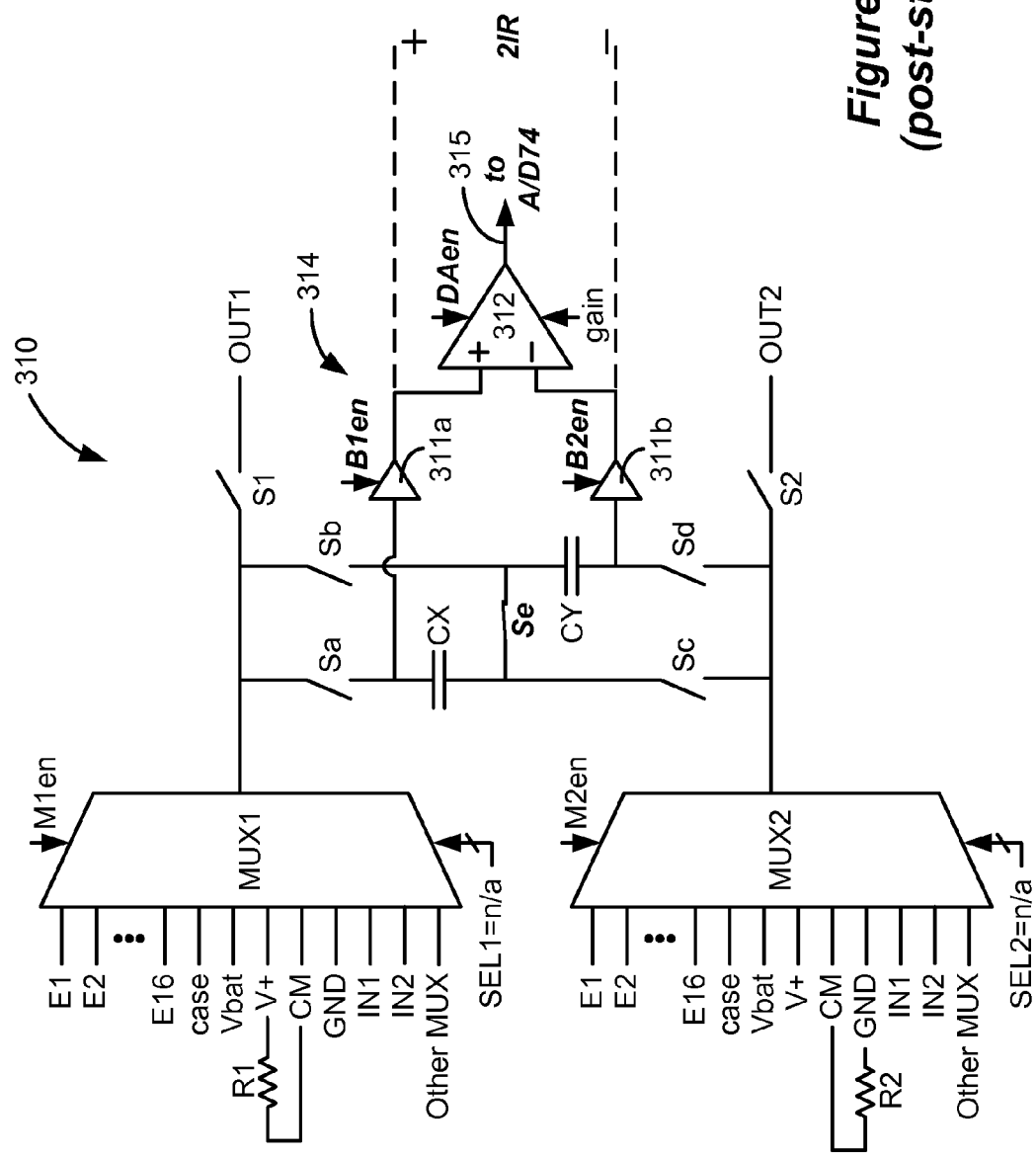
Figure 6E (post-stage)

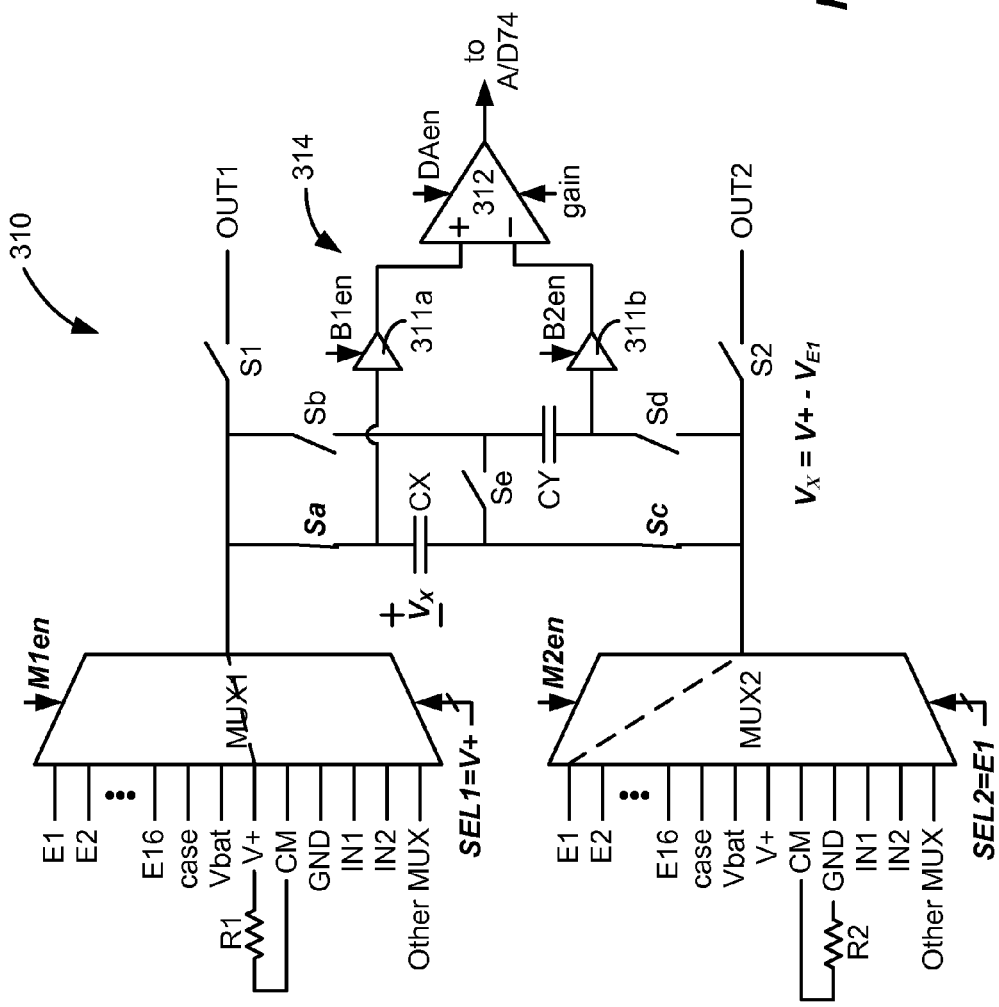
*Figure 7B (stage 1)*

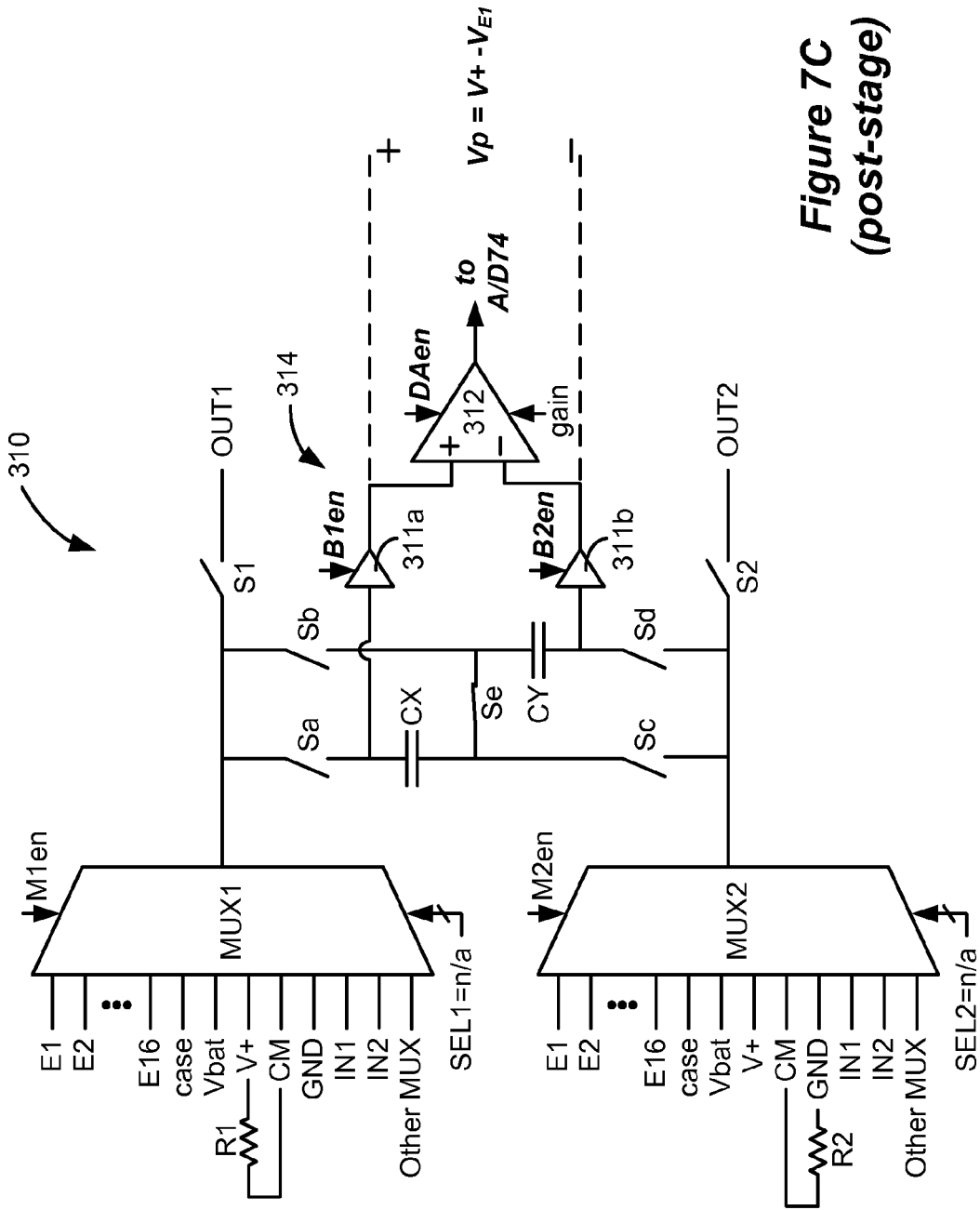
Figure 7C (post-stage)

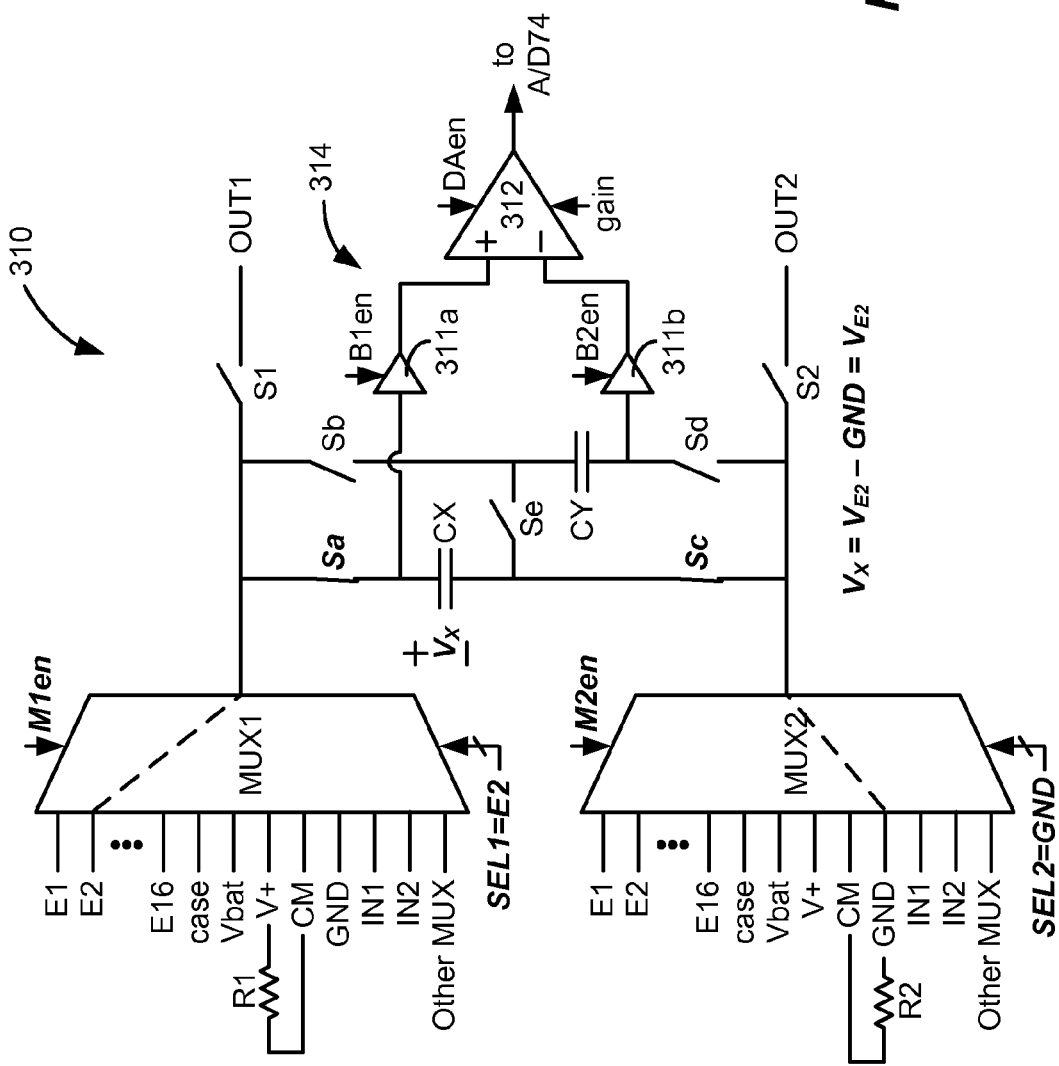
*Figure 7D (stage 1)*

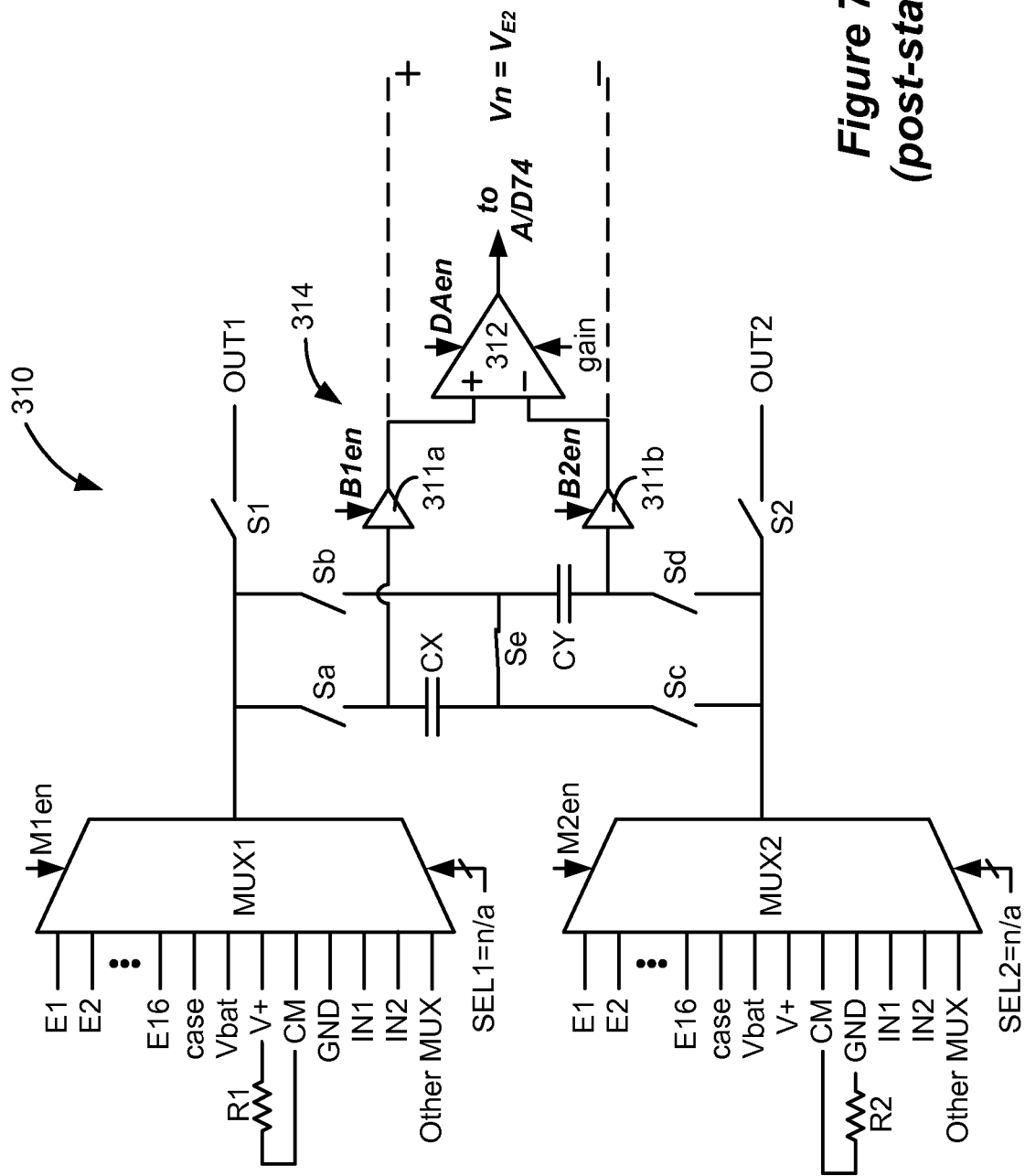
Figure 7E (post-stage)

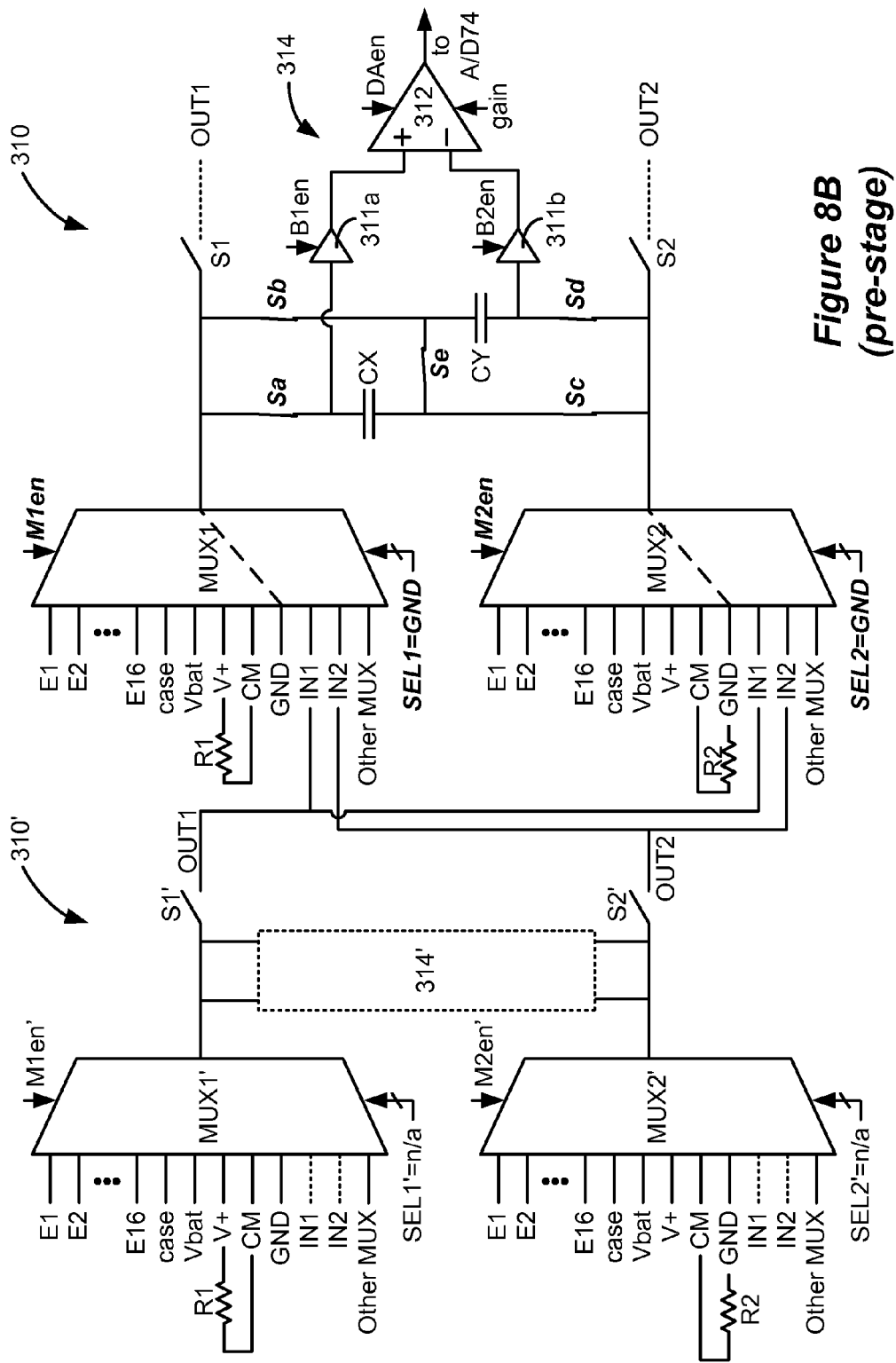
Figure 8B (pre-stage)

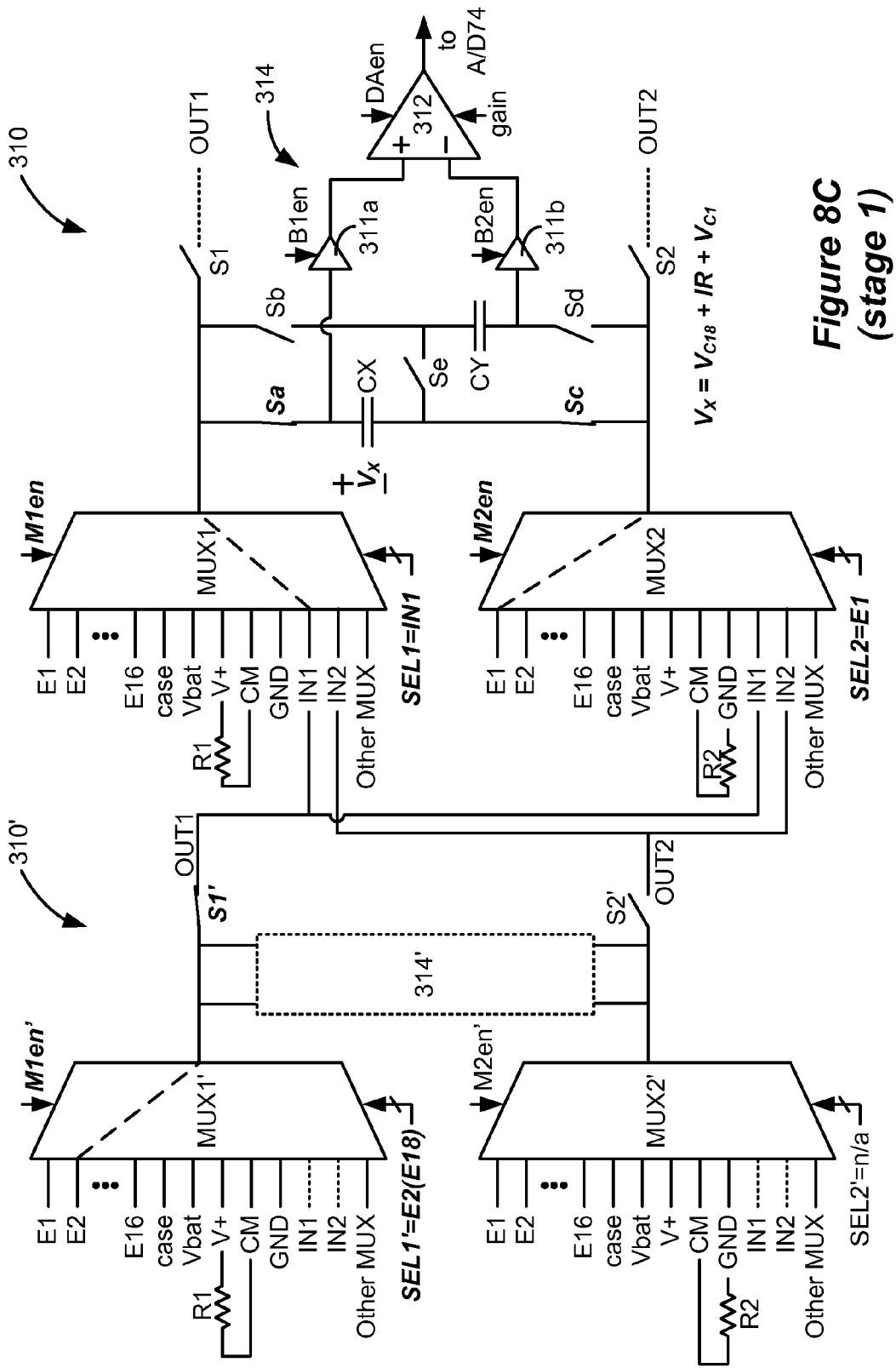
Figure 8C (stage 1)

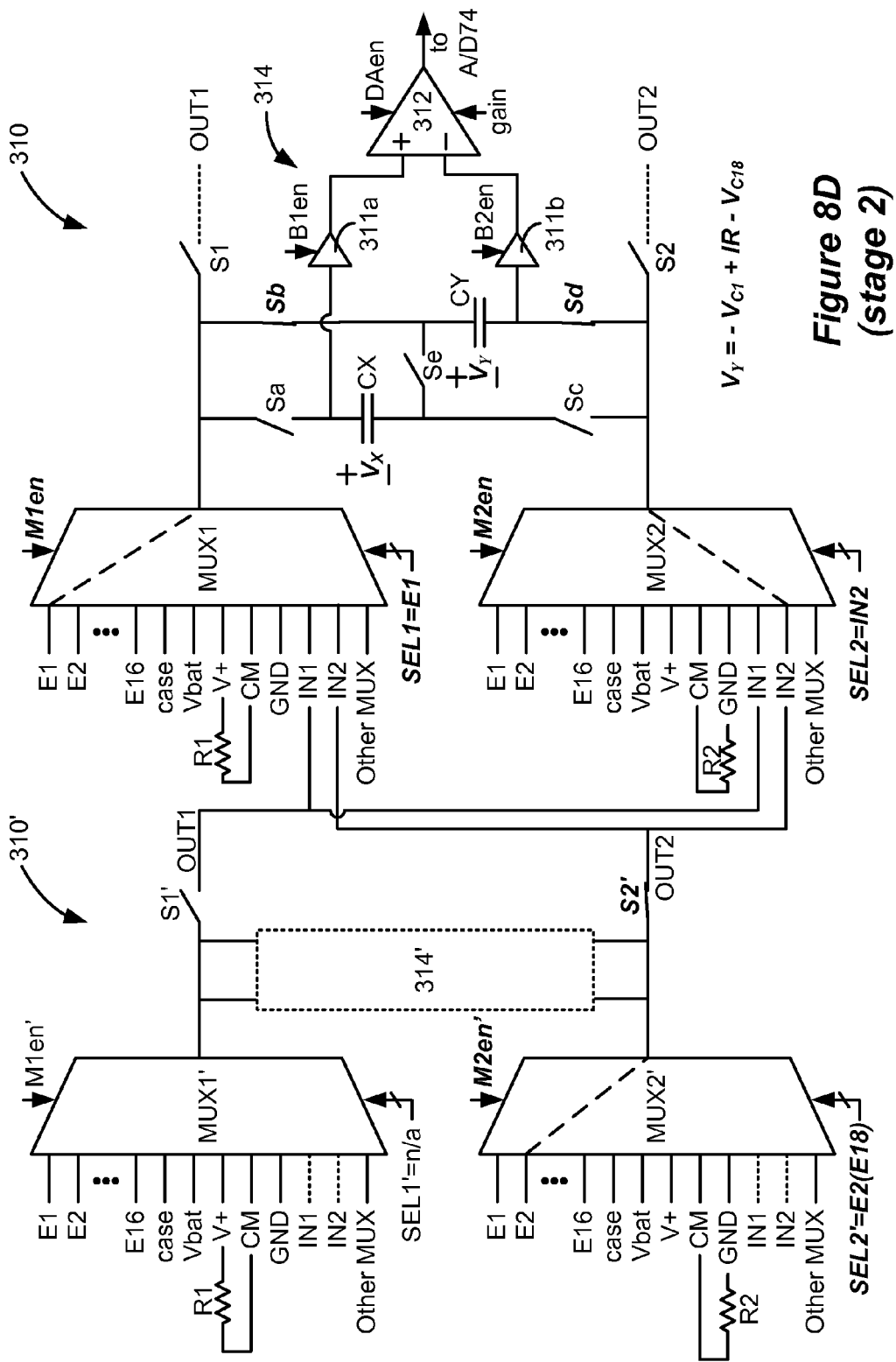
Figure 8D (stage 2)

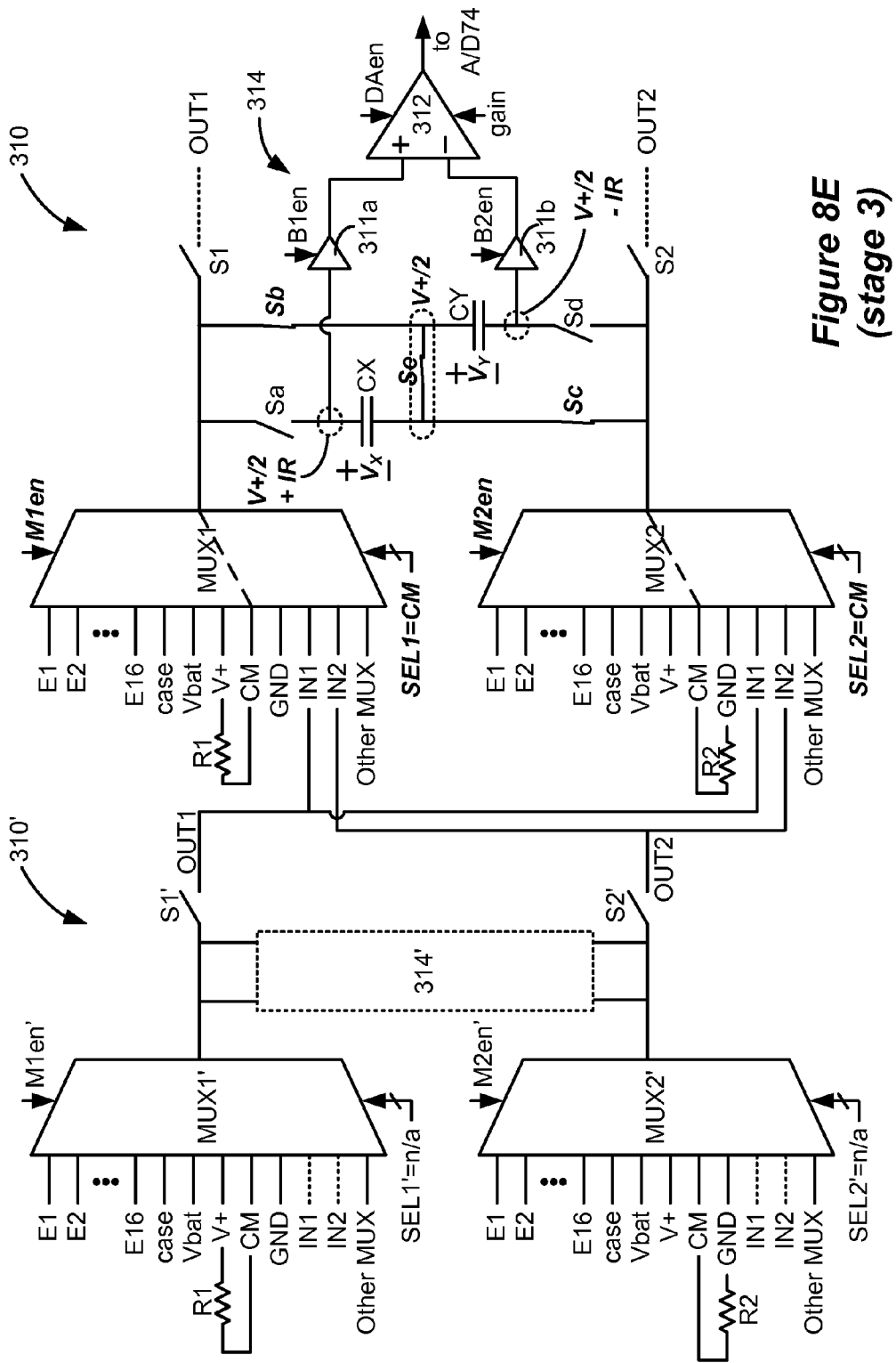
Figure 8E (stage 3)

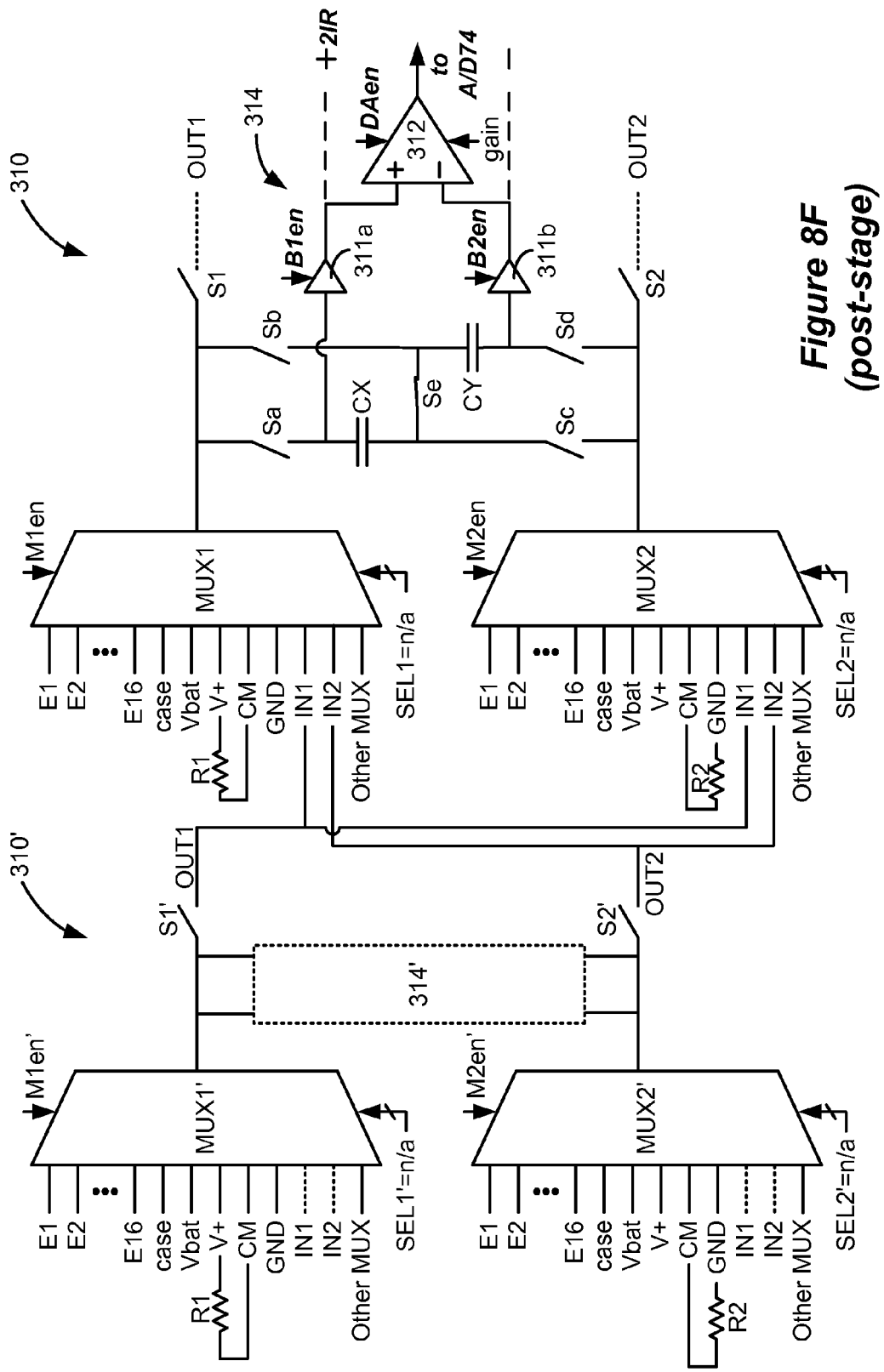
Figure 8F (post-stage)

SAMPLE AND HOLD CIRCUITRY FOR MONITORING VOLTAGES IN AN IMPLANTABLE NEUROSTIMULATOR

CROSS-REFERENCE TO RELATED APPLICATIONS

This is a continuation of U.S. patent application Ser. No. 13/237,172, filed Sep. 20, 2011, which is a non-provisional application of U.S. Patent Application Ser. No. 61/392,600, filed Oct. 13, 2010. Priority is claimed to these applications, and they are incorporated herein by reference in its entirety.

This application is also related to U.S. Patent Application Ser. Nos. 61/392,594 and 61/392,587, both filed Oct. 13, 2010, which are both incorporated herein by reference in their entireties.

FIELD OF THE INVENTION

The present invention relates generally to implantable medical devices, and more particularly to improved circuitry for monitoring voltages in an implantable neurostimulator device.

BACKGROUND

Implantable neurostimulator devices are devices that generate and deliver electrical stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system, such as that disclosed in U.S. Pat. No. 6,516,227. However, the present invention may find applicability in any implantable neurostimulator.

As shown in FIGS. 1A and 1B, a SCS system typically includes an Implantable Pulse Generator (IPG) 100, which includes a biocompatible device case 30 formed of a conductive material such as titanium for example. The case 30 typically holds the circuitry and battery 26 necessary for the IPG to function, although IPGs can also be powered via external RF energy and without a battery. The IPG 100 includes one or more electrode arrays (two such arrays 102 and 104 are shown), each containing several electrodes 106. The electrodes 106 are carried on a flexible body 108, which also houses the individual electrode leads 112 and 114 coupled to each electrode. In the illustrated embodiment, there are eight electrodes on array 102, labeled $E_1$-$E_8$, and eight electrodes on array 104, labeled $E_9$-$E_{16}$, although the number of arrays and electrodes is application specific and therefore can vary. The arrays 102, 104 couple to the IPG 100 using lead connectors 38a and 38b, which are fixed in a non-conductive header material 36, which can comprise an epoxy for example.

As shown in FIG. 2, the IPG 100 typically includes an electronic substrate assembly 14 including a printed circuit board (PCB) 16, along with various electronic components 20, such as microprocessors, integrated circuits, and capacitors mounted to the PCB 16. Two coils (more generally, antennas) are generally present in the IPG 100: a telemetry coil 13 used to transmit/receive data to/from an external controller 12; and a charging coil 18 for charging or recharging the IPG's battery 26 using an external charger 50. The telemetry coil 13 is typically mounted within the header 36 of the IPG 100 as shown, and may be wrapped around a ferrite core 13'.

As just noted, an external controller 12, such as a handheld programmer or a clinician's programmer, is used to wirelessly send data to and receive data from the IPG 100. For example, the external controller 12 can send programming data to the IPG 100 to dictate the therapy the IPG 100 will provide to the patient. Also, the external controller 12 can act as a receiver of data from the IPG 100, such as various data reporting on the IPG's status. The external controller 12, like the IPG 100, also contains a PCB 70 on which electronic components 72 are placed to control operation of the external controller 12. A user interface 74 similar to that used for a computer, cell phone, or other hand held electronic device, and including touchable buttons and a display for example, allows a patient or clinician to operate the external controller 12. The communication of data to and from the external controller 12 is enabled by a coil (antenna) 17.

The external charger 50, also typically a hand-held device, is used to wirelessly convey power to the IPG 100, which power can be used to recharge the IPG's battery 26. The transfer of power from the external charger 50 is enabled by a coil (antenna) 17'. The external charger 50 is depicted as having a similar construction to the external controller 12, but in reality they will differ in accordance with their functionalities as one skilled in the art will appreciate.

Wireless data telemetry and power transfer between the external devices 12 and 50 and the IPG 100 takes place via inductive coupling, and specifically magnetic inductive coupling. To implement such functionality, both the IPG 100 and the external devices 12 and 50 have coils which act together as a pair. In case of the external controller 12, the relevant pair of coils comprises coil 17 from the controller and coil 13 from the IPG 100. In case of the external charger 50, the relevant pair of coils comprises coil 17' from the charger and coil 18 from the IPG 100. As is well known, inductive transmission of data or power can occur transcutaneously, i.e., through the patient's tissue 25, making it particularly useful in a medical implantable device system. During the transmission of data or power, the coils 17 and 13, or 17' and 18, preferably lie in planes that are parallel, along collinear axes, and with the coils as close as possible to each other. Such an orientation between the coils 17 and 13 will generally improve the coupling between them, but deviation from ideal orientations can still result in suitably reliable data or power transfer.

The concurrent application incorporated above—with which the reader is assumed familiar, and which is not fully discussed here—discloses an improved architecture for an IPG 295 as shown in FIGS. 3A and 3B. The improved IPG architecture involves integration of various IPG functional circuit blocks (FIG. 3B) on a single integrated circuit (IC) 300 via a bus 297 governed by a communication protocol. To communicate with the bus 297 and to adhere to the protocol, each circuit block includes bus interface circuitry 215 (FIG. 3B) adherent with that protocol. Because each circuit block complies with the protocol, any given circuit block can easily be modified or upgraded without affecting the design of the other blocks, facilitating debugging and upgrading of the IPG system 290. Moreover, because the centralized bus 297 can be taken off the integrated circuit 300, extra circuitry can easily be added off chip to modify or add functionality to the IPG 295.

For example, and as shown in FIG. 3A, two electrode driver ICs 300 and 300' are daisy chained to double the electrode capacity in the IPG 295, i.e., from 16 to 32 electrodes as shown. ICs 300 acts as a master while IC 300' acts as its slave, with discrimination between the two being enabled by chip select signals CS_m and CS_s respectively. Microcontroller 305 provides for control of functions in the system 290 not handled by various circuit blocks in the ICs 300 and 300', and otherwise generally acts as the system's master. However, it is not necessary that ICs 300 be daisy chained pursuant to the strategies disclosed in the concurrent application, and instead an IPG system may use only one such IC 300.

Referring to FIG. 3B, each of the circuit blocks in IC 300 performs a particular function in an IPG. For example, telemetry block 62 couples to the IPG telemetry coil 13, and includes transceiver circuitry for communicating with the external controller 12 (FIG. 2). The charging/protection block 64 couples to the IPG charging coil 18, and contains circuitry for rectifying power received from the external charger 50 (FIG. 2), and for charging the power source (battery) 26 in a controlled fashion. Stimulation circuit block 175 is coupled to the electrodes E1-E16 and includes circuitry for setting the program (magnitude, and polarity) for the stimulation pulses appearing at those electrodes. Stimulation circuit block 175 also includes the drivers for the electrodes, with a Digital-to-Analog Converter (DAC) 82 being responsive to the stimulation program to supply current to the specified electrodes via current source and sink circuitry. Notice that the electrodes E1-E16 are connected to off-chip decoupling capacitors C1-CN prior to connection to the corresponding electrodes 106 on the leads 102 and 104 (FIG. 1A); such decoupling capacitors C1-CN prevents direct DC current injection from the IPG into the patient, which is advisable for safety, but otherwise such decoupling capacitors do not significantly affect stimulation performance.

The compliance voltage (V+) generator block 320 generates a compliance voltage, V+, which is used by the current sources (DAC 82) in the stimulation circuitry block 175. The clock generator block 330 generates the communications clocks to synchronize communications on the bus 297, as well other clocks needed internal to the IC 300. The master/slave (M/S) controller 350 informs the IC 300 whether it is acting in a master or slave capacity should the IC 300 be operating in a system with more than one IC 300, such as is shown in FIG. 3A. Interrupt controller block 173 receives various interrupts from other circuit blocks, which because of their immediate importance are received independent of the bus 297. Internal controller 160 acts as the master controller for all other circuit blocks. EPROM block 177 caches any relevant data in the system (such as log data), and additional memory 66 can also be provided off-chip via a serial interface block 167. External terminals 202 (e.g., pins, bond pads, solder bumps, etc.) are used to carry signals to and from the IC 300.

Of particular relevance to this disclosure are the sample and hold block 310 and the Analog-to-Digital (A/D) block 74. As shown in FIG. 3B, the sample and hold block 310 receives various analog signals via an analog bus 192, such as the voltages appearing at the electrodes E1-E16, the battery voltage (Vbat), the compliance voltage (V+), etc. The goal of the sample and hold block 310—as its name suggests—is to sample selected ones of the various analog bus 192 signals, and to hold then so their voltage magnitudes can be resolved. The resolved analog voltages are then sent from the sample and hold block 310 to the A/D block 74 where they are digitized and sent for interpretation via the bus 297 elsewhere in the IC 300 or microcontroller 305.

It is particularly important to monitor the voltages at the electrodes, either during stimulation or testing. Assessing such voltages is beneficial for many reasons. Knowing the electrode voltages allows the resistance between the electrodes, R, to be calculated, which is useful for a variety of reasons. Also, knowing the voltages present at the electrodes during stimulation can be useful in setting the compliance voltage, V+, at the V+ generator 320 (FIG. 4B) to an appropriate and power-efficient magnitude. See, e.g., U.S. Pat. No. 7,444,181. This disclosure presents improved sample and hold circuitry for the sample and hold block 310 for assessing electrode and other voltages of interest in the IPG.

BRIEF DESCRIPTION OF THE DRAWINGS

FIGS. 6A-6E illustrate operation of the sample and hold circuitry 310 to determine the resistance between electrodes, with each figure showing a different stage of the measurement.

FIGS. 7A-7E illustrate operation of the sample and hold circuitry 310 to determine the voltage drops across the current sources as is useful in setting the compliance voltage for the current sources, with each figure showing a different stage of the measurement.

FIGS. 8A-8F illustrate operation of the sample and hold circuitry 310 to determine the resistance between electrodes in an embodiment in which two daisy-chained ICs are used.

DETAILED DESCRIPTION

Sample and hold circuitry for monitoring electrodes and other voltages in an implantable neurostimulator is disclosed. The sample and hold circuitry in one embodiment contains multiplexers to selected appropriate voltages and to pass them to two storage capacitors during two different measurement phases. The capacitors are in a later stage serially connected to add the two voltages stored on the capacitors, and voltages present at the top and bottom of the serial connection are then input to a differential amplifier to compute their difference. The sample and hold circuitry is particularly useful in calculating the resistance between two electrodes, and is further particularly useful when resistance is measured using a biphasic pulse. The sample and hold circuitry is flexible, and can be used to measure other voltages of interest during biphasic or monophasic pulsing.

Figure 4:
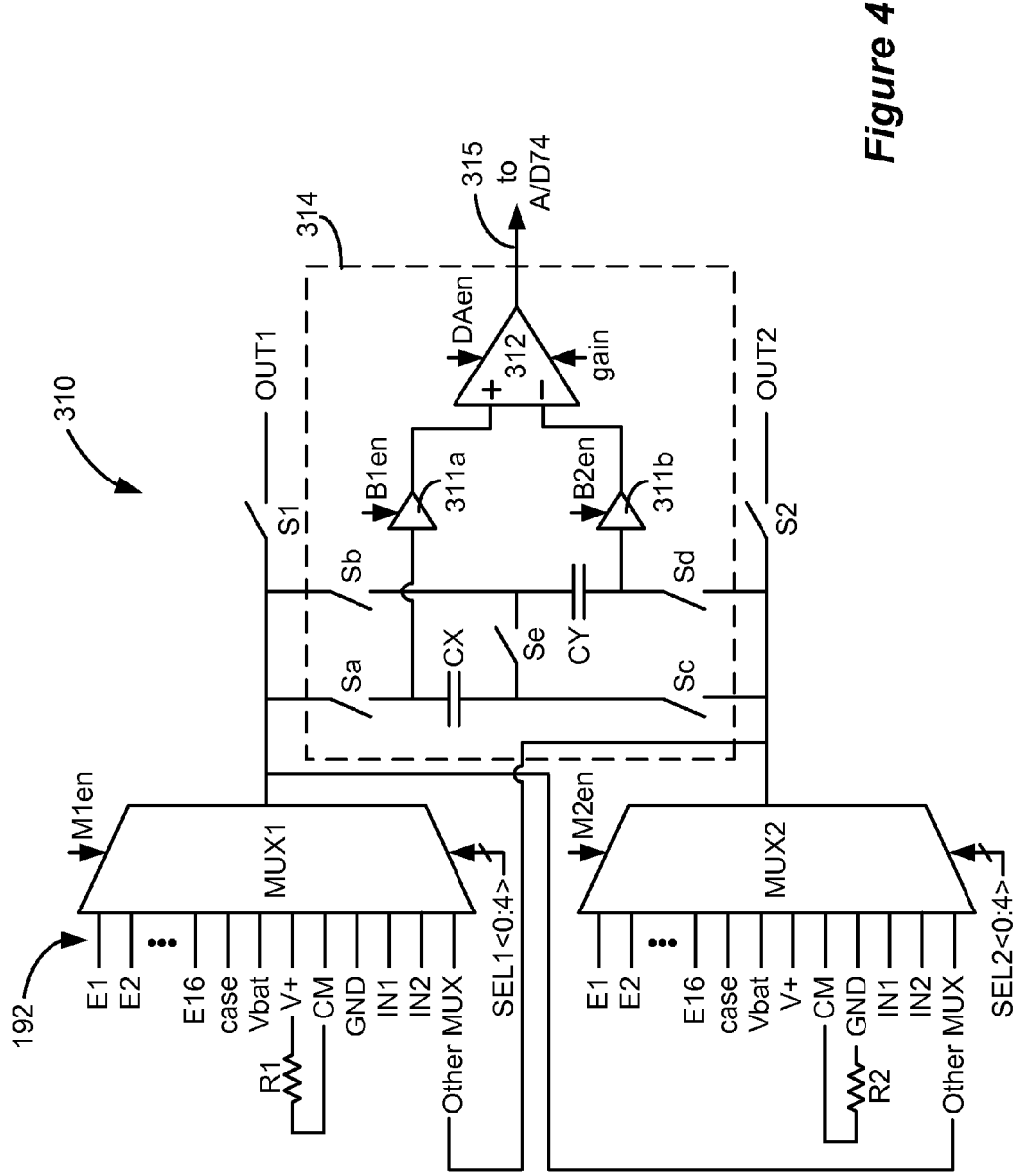
FIG. 4 illustrates an improved sample and hold circuit for monitoring various voltages in the IPG.

An embodiment of improved sample and hold circuitry 310 is shown in FIG. 4. As noted earlier, the sample and hold circuitry 310 selects from various signal on the analog bus 192 so that important voltages in the IC 300 can be monitored. In the disclosed embodiment, selection occurs using two multiplexers, MUX1 and MUX2. The inputs to each MUX are essentially the same and comprise the electrode voltages (E1-E16); the metallic case (case); the battery voltage (Vbat); the compliance voltage used by the DACs 82 (V+); and ground (GND). As will be seen in the examples that follow, MUX1 is generally used to select a higher voltage, such as an anode electrode or a supply voltage (e.g., Vbat or V+), while MUX2 is generally used to select a lower voltage, such as a cathode electrode or ground. An additional common mode input (CM) can be used during voltage monitoring, and the relevance of this input will be described later. Also, the output of each MUX is sent to the other MUX in case it is of interest to select such other output for a given measurement. Because of the wide variety of inputs signals to the MUXes, the sample and hold circuitry 310 is capable of monitoring a wide variety of voltages, thus allowing for the analysis of a wide variety of phenomenon in the IPG, some of which will be explained later. Other analog signals of importance within the IPG may be included as inputs to the MUXes, and the inputs shown should not be understood as exclusive.

Inputs IN1 and IN2, switches S1 and S2, and outputs OUT1 and OUT2, are implicated when more than one IC 300 are daisy chained together, which will be discussed with respect to FIGS. 8A-8F.

MUX1 and MUX2 are enabled by enabled signals M1*en* and M2*en* respectively, and the input selected from each is dictated in accordance with control signals SEL1 and SEL2 respectively. In the embodiment shown, five bits (SELx<0: 4>) are used to select one of the 24 inputs to the MUXes.

Figures 1A, 1B:
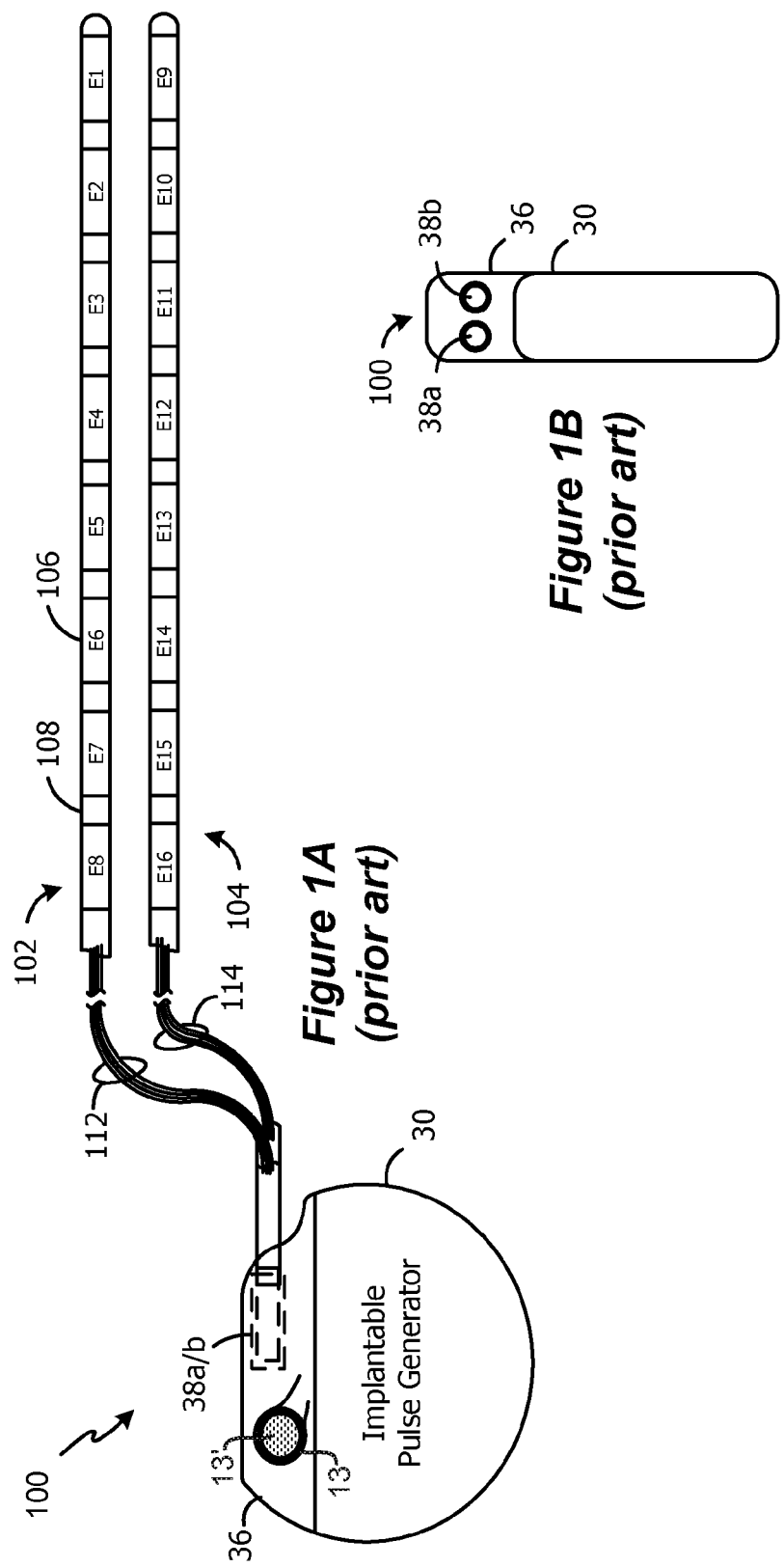
FIGS. 1A and 1B illustrate an implantable pulse generator (IPG), and the manner in which an electrode array is coupled to the IPG in accordance with the prior art.
Figure 2:
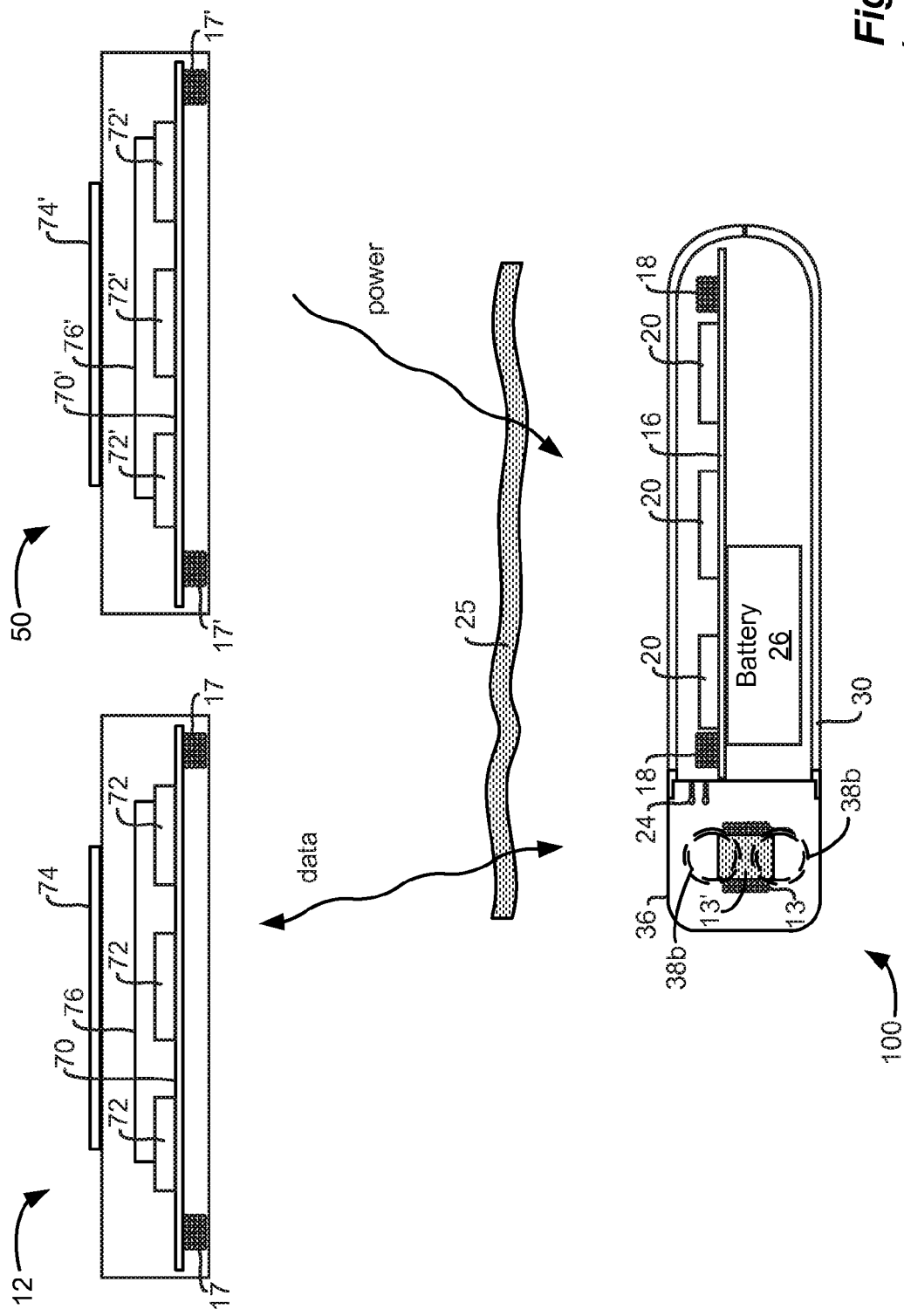
FIG. 2 illustrates an IPG, an external controller, and an external charger in accordance with the prior art.
Figure 3A:
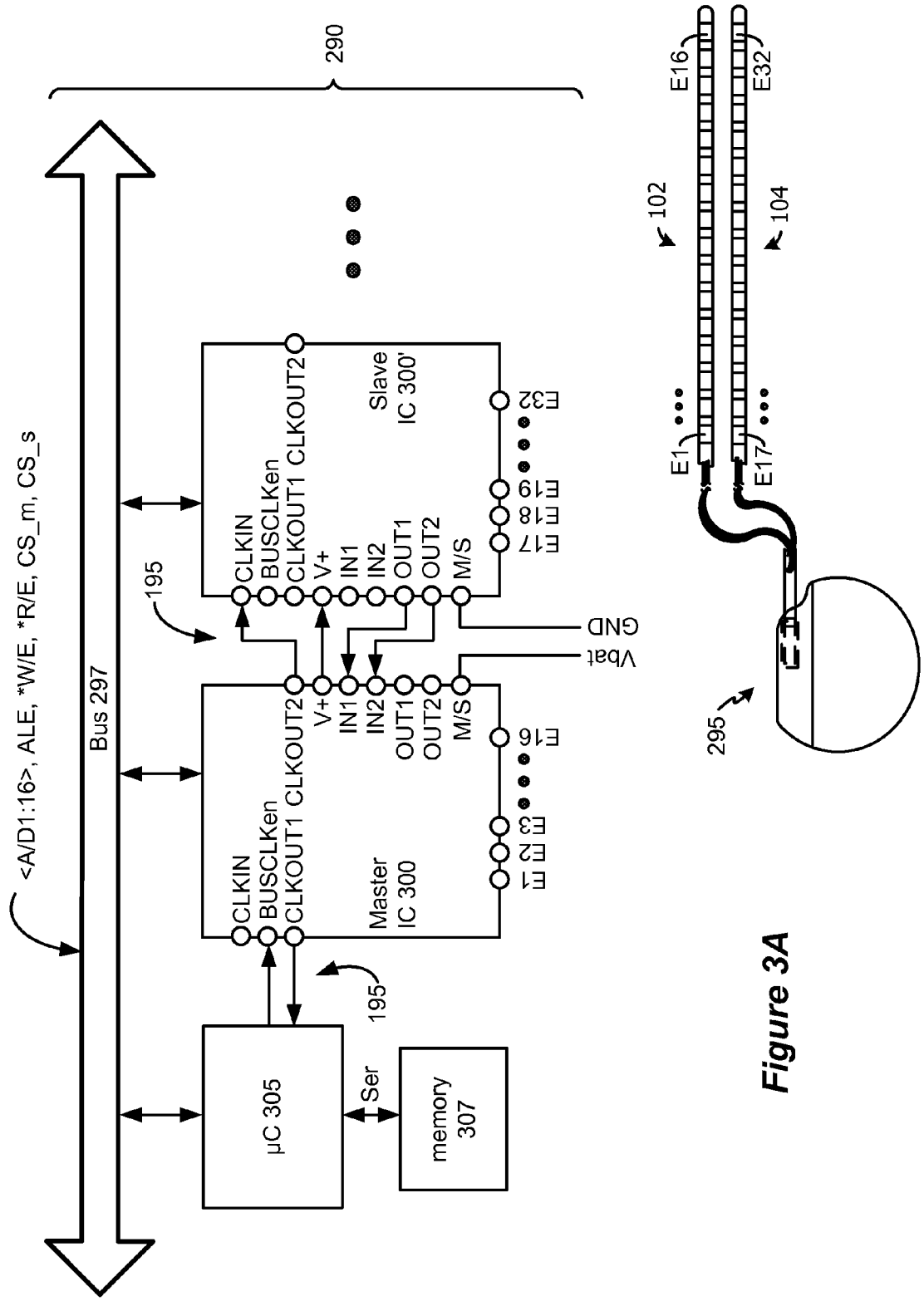
FIGS. 3A-3B illustrate aspects of an IPG architecture disclosed in the concurrent application incorporated above.
Figure 3B:
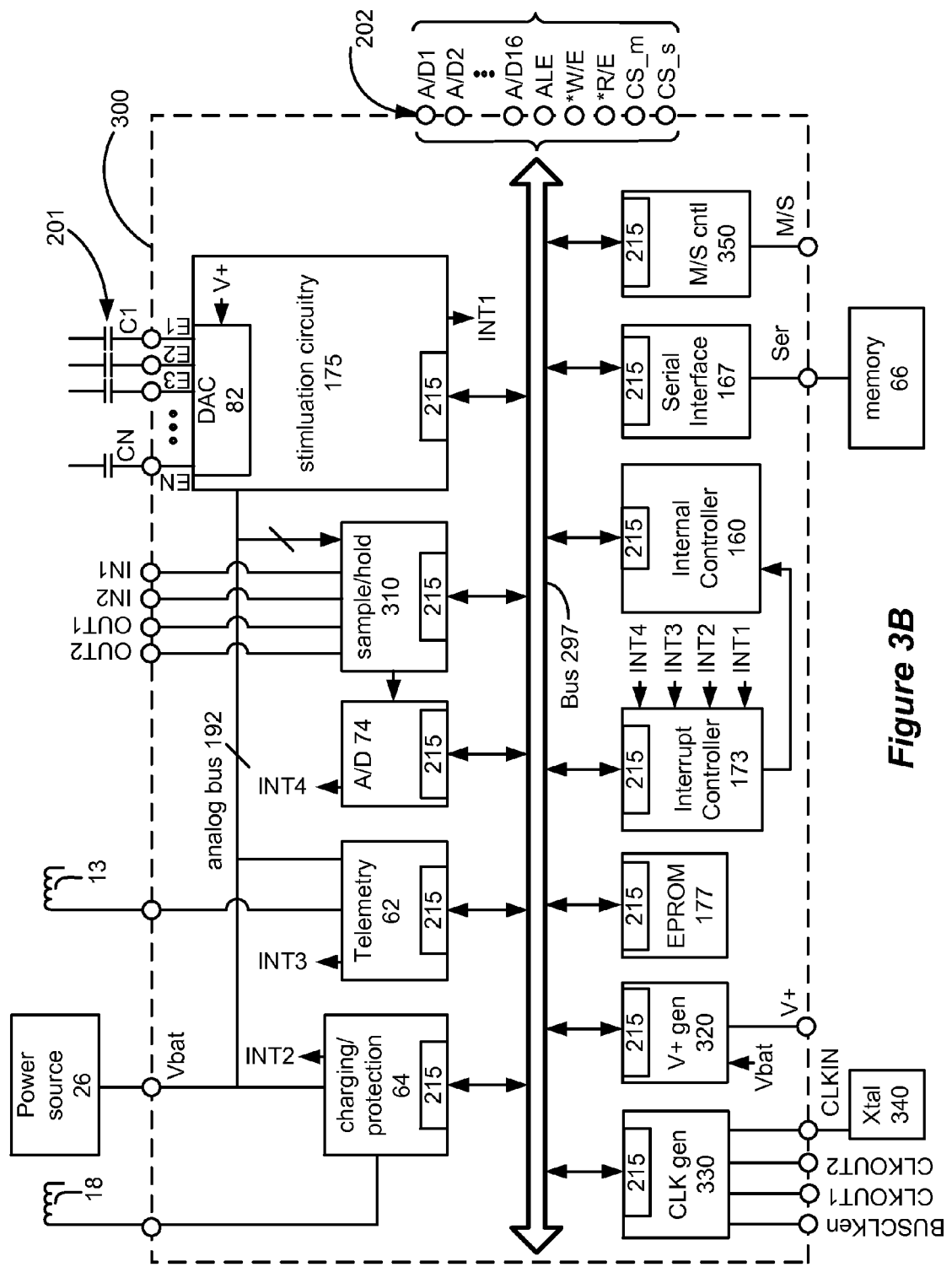

Signals selected by the MUXes are held for resolution by holding circuitry 314. In the embodiment of FIG. 4, holding circuitry 314 comprises two capacitors, CX and CY, a plurality of switches, Sa-Se, and output buffers 311*a* and 331*b* enabled by enable signals B1*en* and B2*en* respectively. Capacitors CX and CY are preferably identical, and may have a capacitance of 4.7 microfarads for example. As will be seen, monitored voltages are impressed or stored on these capacitors CX and CY, with a voltage selected by MUX1 being presented to the top plates of CX and CY, and a voltage selected by MUX2 being presented to the bottom plates of CX and CY. The output of buffers 311*a* and 331*b* are input to a differential amplifier 312, which outputs their difference (i.e., V311*a*-V311*b*) as an analog signal 315. This analog output 315 can in turn be sent to the A/D block 74 (FIG. 3B), where it is digitized and sent elsewhere in the system for analysis, such as the V+ generator 320 (FIG. 3B) or the microcontroller 305. The switches Sa-Se are controlled by control signals (not shown), which may issue from the internal controller 160 (FIG. 3B), the sample/hold block 310 itself of which the switches are a part, the microcontroller 305, or any other logical or convenient control element in the system 290.

Figure 5A:
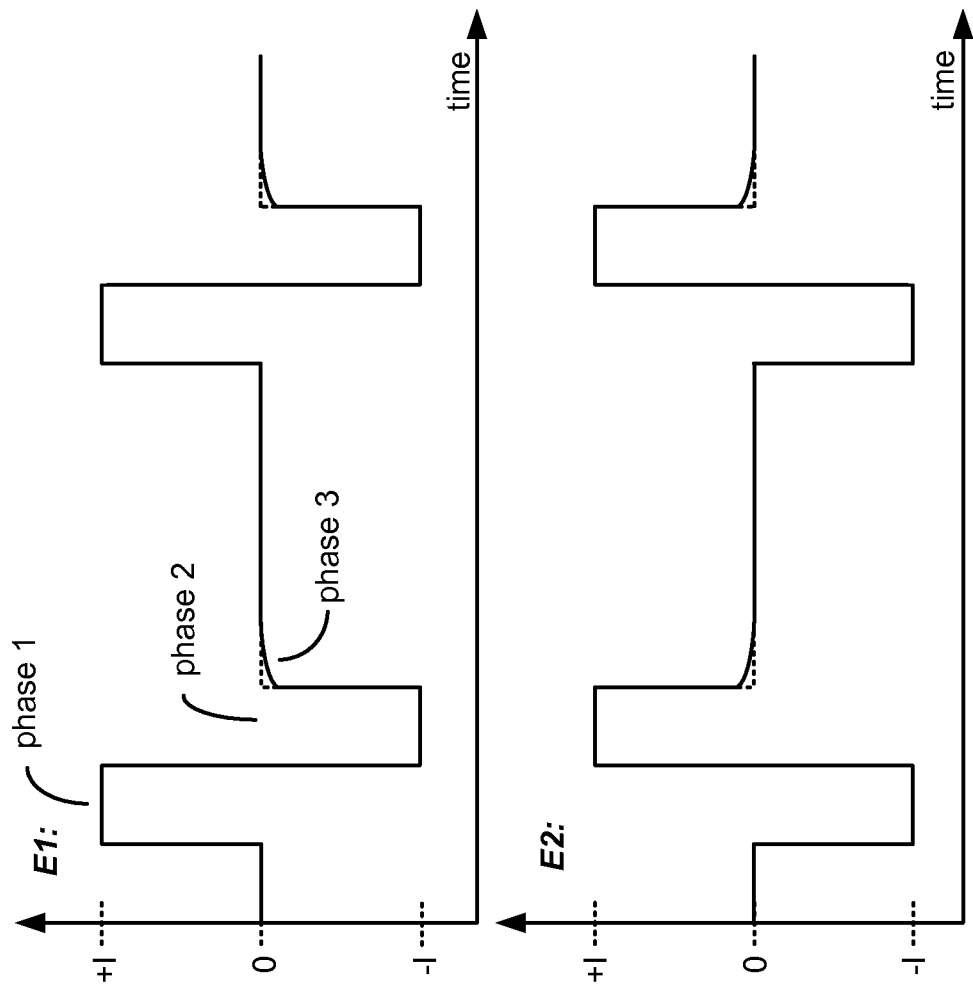
FIGS. 5A-5C illustrate an example in which the sample and hold circuitry of FIG. 4 is used to monitor electrode voltages during provision of a biphasic pulse, and more particularly to measure the resistance between electrodes.
Figure 5B:
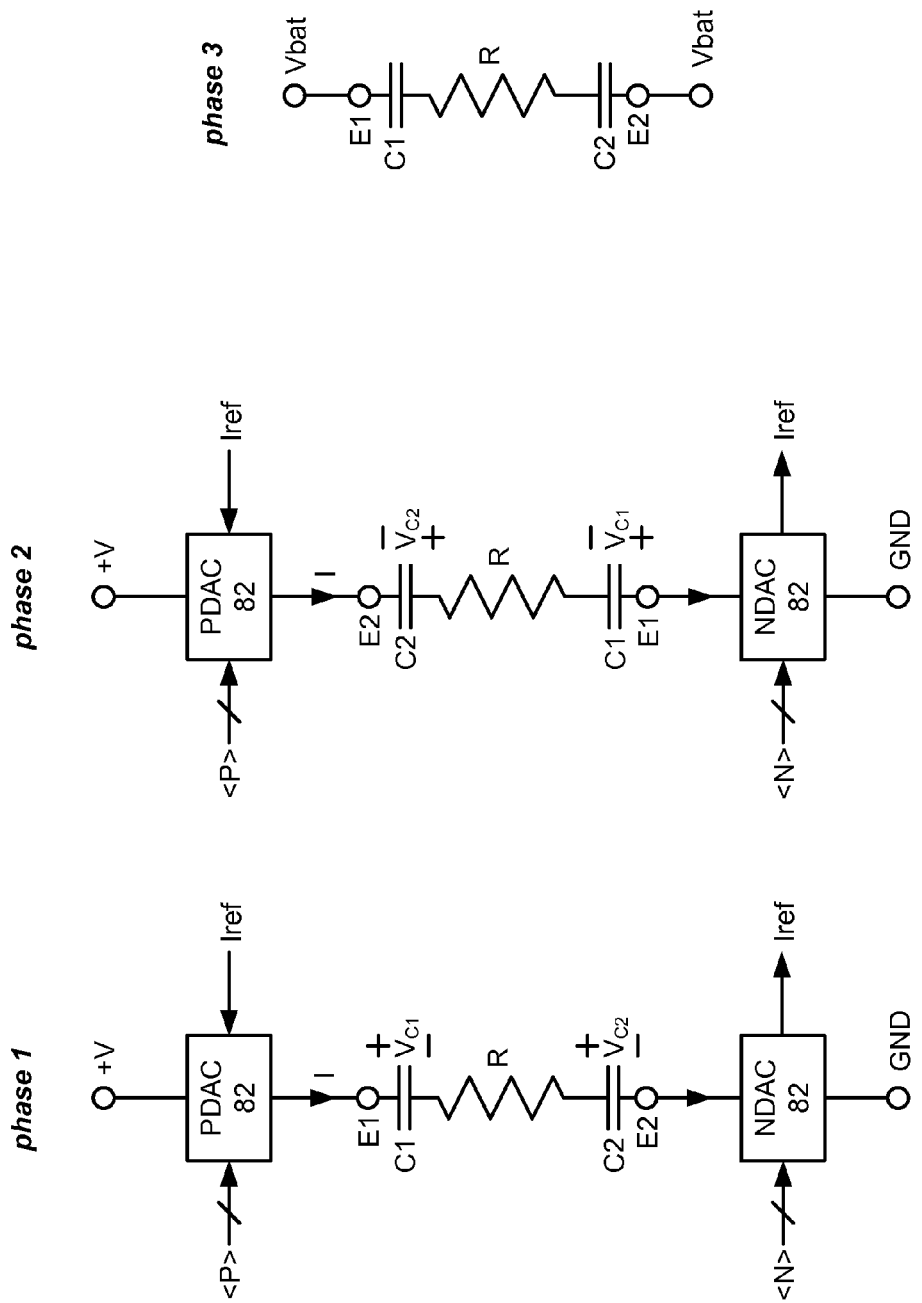
Figure 5C:
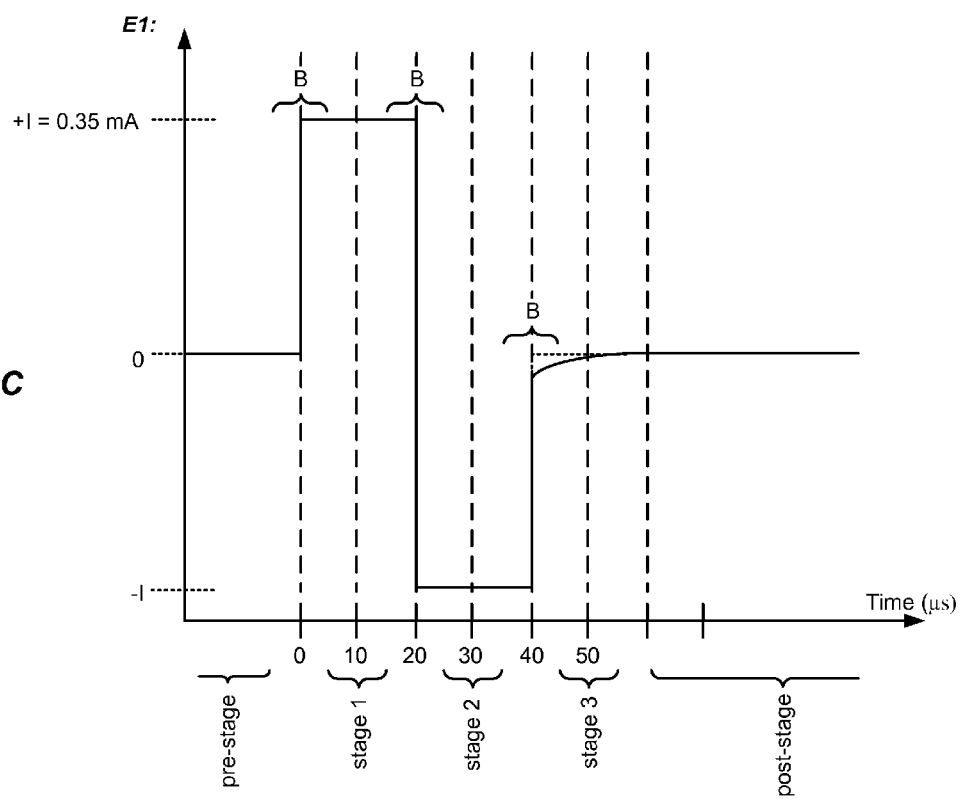

FIGS. 5A-5C illustrate an example in which the sample and hold circuitry 310 of FIG. 4 is used to monitor electrode voltages E1 and E2 during provision of a pulse, and more particularly to measure the resistance between those electrodes. The pulse may comprise a train of pulses as shown, and can comprise an actual therapeutic pulse delivered to the patient. However, in this example, the stimulation pulse is a test pulse used to determine resistance, and while administered to a patient, does not necessarily comprise patient therapy.

In this example, and as shown in FIGS. 5A and 5B, the pulse is biphasic, meaning that at each electrode a primary pulse (phase 1) is followed by a pulse of opposite polarity (phase 2). Biphasic pulsing, and rationales for using such a pulsing strategy, are well known in the neurostimulator art. During phase 1, electrode E1 comprises the anode for sourcing a current I, while electrode E2 comprises the cathode for sinking that current I. Resistance R represents the resistance between the electrodes E1 and E2, is a function of many variables, including importantly the resistance of patient's tissue. During phase 2, the polarity is flipped, such that electrode E2 now source current I, while electrode E1 sinks that current I. To the extent that any residual charge remains, a passive recovery phase (phase 3) follows the opposite-polarity pulse to recover any residual charge that has been injected into the patient. Passive recovery is usually affected by coupling the stimulating electrodes (E1, E2) to a reference node, such as the battery voltage (Vbat). Note that each of the biphasic pulses at each of the electrodes could be considered as two pulses at the two different phases. The duration of phases 1 and 2 are preferably the same.

The currents (+I, −I) appearing at each electrode are set by DACs 82 (FIG. 5B), which as noted earlier comprises part of the stimulation circuitry 175. As is known, the DACs 82 provide the desired current based on digital control signals (<P>, <N>), which control signals specify the amount that a reference current, Iref, is to be amplified. A DAC used as the anodic source is called a PDAC, while a DAC used as the cathodic sink is called a NDAC. See, e.g., U.S. Patent Publication 2007/0038250, for further details concerning the specifics of PDAC and NDAC circuitry useable in IPG such as IPG 295.

The off-chip decoupling capacitors C1 and C2 respectively connected to electrodes E1 and E2 are also shown in FIG. 5B, and note that each carries a parasitic voltage $V_{C1}$ and $V_{C2}$ respectively. These parasitic voltages are DC voltages, and arise from the inability to remove charge from the decoupling capacitors C1 and C2: such parasitic voltages can't be completely removed because the potential of the patient's tissue (at resistance R) cannot be controlled. As will be seen, a significant benefit of the disclosed sample and hold circuit 310 is its ability to cancel these parasitic voltages, thereby allowing for a more accurate resistance measurement. Note that while the polarity of stimulation changes between phases 1 and 2, the polarity of the parasitic voltage $V_{C1}$ and $V_{C2}$ relative to the electrodes does not. Even if decoupling capacitors are not used in a particular IPG architecture, parasitic capacitances will exist at the electrode tissue interface, and such parasitic capacitances will also carry parasitic voltages $V_{C1}$ and $V_{C2}$. Such parasitic capacitances can be viewed as included in the decoupling capacitors C1 and C2 to the extent they are used.

FIG. 5C shows further details of the biphasic pulse as particularly useful in measuring the resistance between electrodes, and illustrates various stages of operation of the sample and hold circuitry 310. (Only the pulse at E1 is shown for simplicity). As shown, the pulse has a magnitude ranging from −0.35 to 0.35 mA, and a total duration of 40 microseconds. A pre-stage precedes phase 1, ending 5 microseconds prior to the start of the phase 1 pulse at t=0. Stage 1 occurs between 5-15 microseconds during the phase 1 pulse, and stage 2 between 25-35 microseconds during the phase 2 pulse. Stage 3 occurs 5 microseconds after cessation of the pulse at 45 microseconds during phase 3 recovery. Between each of these stages are blanking periods (B), during which all of the switches Sa-Se in the sample and hold circuit 310 are opened. As will be appreciated shortly, such blanking periods allow the sample and hold circuit 310 to operate without conflict between the stages.

FIGS. 6A-6E show operation of the sample and hold circuitry 310 to determine the resistance between electrodes E1 and E2, with each figure showing a different stage of the measurement. Active signals in each of these Figures are bolded and italicized to better understand circuit operation. Due to the bus-based nature of communication in the IC 300, it should be understood that the resistance measurement that follows will involve sending bus commands to appropriate addresses in the sample and hold circuitry 310 at appropriate times. Because such addressing is discussed in detail in the above-incorporated concurrent application, such details are not repeated here.

FIG. 6A shows configuration of the sample and hold circuitry 310 pre-stage, i.e., in preparation of the measurements to follow. During this pre-stage, the capacitors are discharged. This occurs by choosing the ground input at both MUX1 and MUX2, and by closing all of the switches Sa-Se in the holding circuitry 314. This shorts both plates of the capacitors C1 and C2 to ground, as well as shorts the two ground signals being passed by the MUXes together. This ensures that capacitors CX and CY have no residual voltages across them prior to taking measurements.

After a blanking period, FIG. 6B shows measurement of the electrode voltages E1 and E2 during stage 1. Because E1 acts as the anode during this phase, and thus would be biased to a higher voltage, it is selected by the top MUX1; because E2 acts as the cathode, and thus would be biased to a lower voltage, it is selected by bottom MUX2. During stage 1, the voltage $V_X$ between electrodes E1 and E2 is impressed or stored on capacitor CX, which voltage will equal the sum of the two parasitic voltages across the decoupling capacitors C1 and C2 ($V_{C1}+V_{C2}$) and the drop across the patient's tissue (IR), i.e., $V_X=V_{C1}+IR+V_{C2}$. Voltage $V_X$ is impressed across capacitor CX by closing switches Sa and Sc, while leaving other switches Sb, Sd, and Se open. Note that leaving switches Sb, Sd, and Se open isolates capacitor CY, whose voltage drop remains 0 by virtue of being grounded during the pre-stage. Referring again to FIG. 5C, stage 1 begins at approximately 5 microseconds and ends at 15 microseconds, therefore allowing capacitor CX to be written to during this 10 microsecond period.

After another blanking period, FIG. 6C shows measurement of the electrode voltages E1 and E2 during stage 2. Because E2 acts as the anode during this phase, and thus would be biased to a higher voltage, it is selected by the top MUX1; because E1 acts as the cathode, and thus would be biased to a lower voltage, it is selected by bottom MUX2. During stage 2, the voltage $V_Y$ between electrodes E2 and E1 is impressed or stored on capacitor CY, which voltage will again will equal the sum of the two parasitic voltages across the decoupling capacitors C1 and C2 and the drop across the patient's tissue (IR). However, because the polarity of stimulation is reversed in phase 2, these parasitic voltages, which remain unchanged from phase 1, are now subtracted, such that $V_Y=-V_{C2}+IR-V_{C1}$. Voltage $V_Y$ is impressed across capacitor CY by closing switches Sb and Sd, while leaving other switches Sa, Sc, and Se open. Note that leaving switches Sa, Sc, and Se open isolates capacitor CX, whose voltage remains $V_X$ by virtue of the earlier stage 1 measurement. Referring again to FIG. 5C, stage 2 begins at approximately 25 microseconds and ends at 35 microseconds, therefore allowing capacitor CY to be written to during this 10 microsecond period.

Figure 6D:
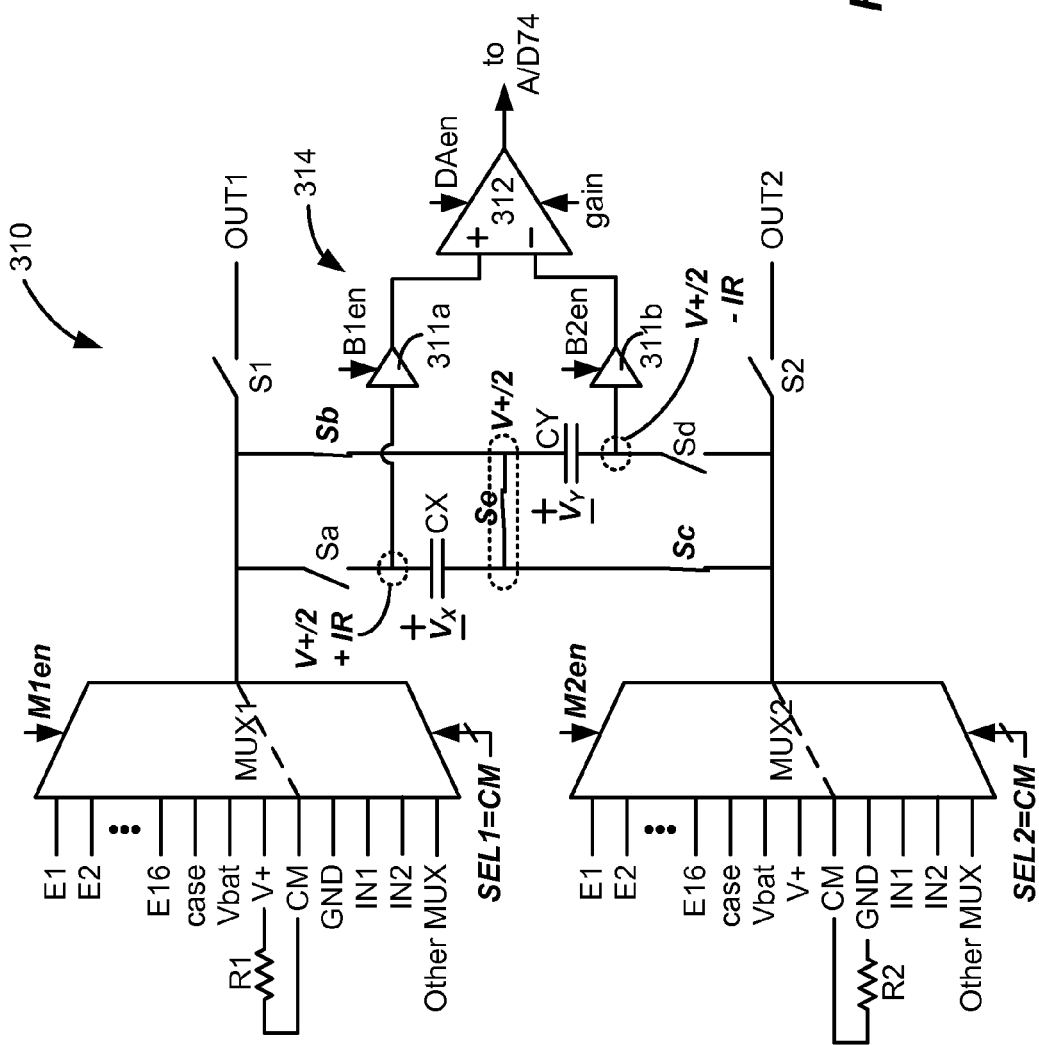

After yet another blanking period, FIG. 6D shows that in stage 3 capacitors CX and CY are connected in series and are provided a reference voltage via the common mode inputs to the MUXes. The capacitors are connected in series by closing switch Se. This creates across the series-connected capacitors a voltage equal to the sum of the previously-stored $V_X$ and $V_Y$ values, namely 2IR. Notice that the parasitic voltages across the decoupling capacitors, $V_{C1}$ and $V_{C2}$, are canceled by this series addition, thus removing them from the measurement, which as noted earlier improves the measurement's accuracy. Additionally, the common node between the capacitors CX and CY is set to a reference voltage of V+/2. This occurs by selecting the common mode inputs, CM, at each of the MUXes, and by closing switches Sb and Sc. Notice that the common mode inputs are wired differently at the MUXes: the common mode input at MUX1 is coupled to the compliance voltage V+ via a resistor R1, while the common mode input at MUX2 is coupled to ground via a resistor R2. In the example shown, R1 and R2 are identical, and of a relatively high value on the order of 250 k-ohm each. When both common mode inputs are selected and shorted at the common node between the capacitors via switches Sb and Sc, R1 and R2 form a voltage divider between V+ and ground, resulting in the common mode voltage of V+/2. Because the 2IR voltage across the series-connected capacitors is preserved, the effect is to present a voltage of (V+/2)+IR to the top buffer 311a, and a voltage of (V+/2)−IR to the bottom buffer 311b.

After yet another blanking period, FIG. 6E shows the post-stage in which the measured and processed voltages are passed to the differential amplifier 312. At this stage, the MUXes are not used, and in fact are isolated from the holding circuitry 314 by opening switches Sa-Sd. Switch Se is closed to maintain the serial connection between the capacitors CX and CY, and the output buffers 311a and 311b are enabled by enable signals B1en and B2en respectively to pass the voltages at the ends of the serial connection of CX and CY to the inputs of the differential amplifier 312. The differential amplifier is also enabled by enable signal DAen to produce at its output 315 an analog voltage representative of the difference at its inputs, i.e., [(V+/2)+IR]−[(V+/2)−IR], or 2IR. Differential amplifier 312 is powered by the compliance voltage V+, and so setting the differential amplifier's input common mode to V+/2 in stage 3 (FIG. 6D) increases the differential amplifier's dynamic range.

Output 315 is thereafter sent to the A/D block 74 (FIG. 3B), where it is digitized and stored. From there, the microcontroller 305 can read the digitized value by addressing the value as stored at the A/D block 74, and can process it to determine the resistance between electrodes E1 and E2. Because the current I is known, the resistance is calculated in the microcontroller 305 by dividing the digitized value by 2I.

It should be noted that the pulses also cause AC charging of the decoupling capacitors C1 and C2, resulting in relatively small voltages across the same. As one skilled will recognize, such AC voltages will be proportional to the current I and the pulse width, and inversely proportional to the capacitance of the decoupling capacitors. Such AC voltages are distinct from the DC parasitic voltages $V_{C1}$ and $V_{C2}$ discussed earlier. Unlike the DC parasitic voltages, any AC voltages across the decoupling capacitors C1 and C2 will match the polarity of the stimulation during a given phase, and may not cancel out of the measurement as do the DC parasitic voltages, resulting in an voltage offset in the overall measurement, i.e., the voltage as sent to the A/D block 74. However, any such AC voltages are comparatively small, are calculable, and can be normalized out of the resistance measurement. For example, using the example biphasic pulse as described in FIG. 5C, the offset to the measured voltages caused by AC charging of the decoupling capacitors equals about 3 mV, and this small amount can be digitally subtracted from the measured voltage in the microcontroller 305 to even further improve measurement accuracy and the overall resistance calculation.

Once the resistance measurement is completed, it can be repeated on a subsequent pulse in the pulse train. Taking repeated measurements between the same pairs of electrodes allows the measured values to be averaged over time, which may improve its accuracy. Additionally, once the resistance is measured between two of the electrodes (e.g., E1 and E2), further resistance measurements can then be taken between different pairs of electrodes (e.g., E2 and E3, E3 and E4, E1 and E3, E1 and E4, etc.). Although beyond the scope of this disclosure, knowing the resistance between the electrodes is of value in improving the safety and functionality of the IPG.

As noted earlier, knowing the voltages present at the electrodes during stimulation can be useful in setting the compliance voltage, V+, at the V+ generator 320 (FIG. 3B) to an appropriate and power-efficient magnitude. In particular, and as discussed in U.S. Pat. No. 7,444,181, it can be particularly useful to know the voltage drop appearing across the current sources and sinks, i.e., the PDACs and NDACs, which voltage drops can only be known in part by monitoring the electrode voltages used during stimulation. By monitoring these voltage drops, the compliance voltage V+ can be set at a magnitude that is sufficient to deliver the required therapeutic current without loading, but not excessively high so as to waste power in the IPG. The disclosed sample and hold circuit 310 allows these voltage drops to be measured, and FIG. 7A-7E Illustrate how this occurs.

Figure 7A:
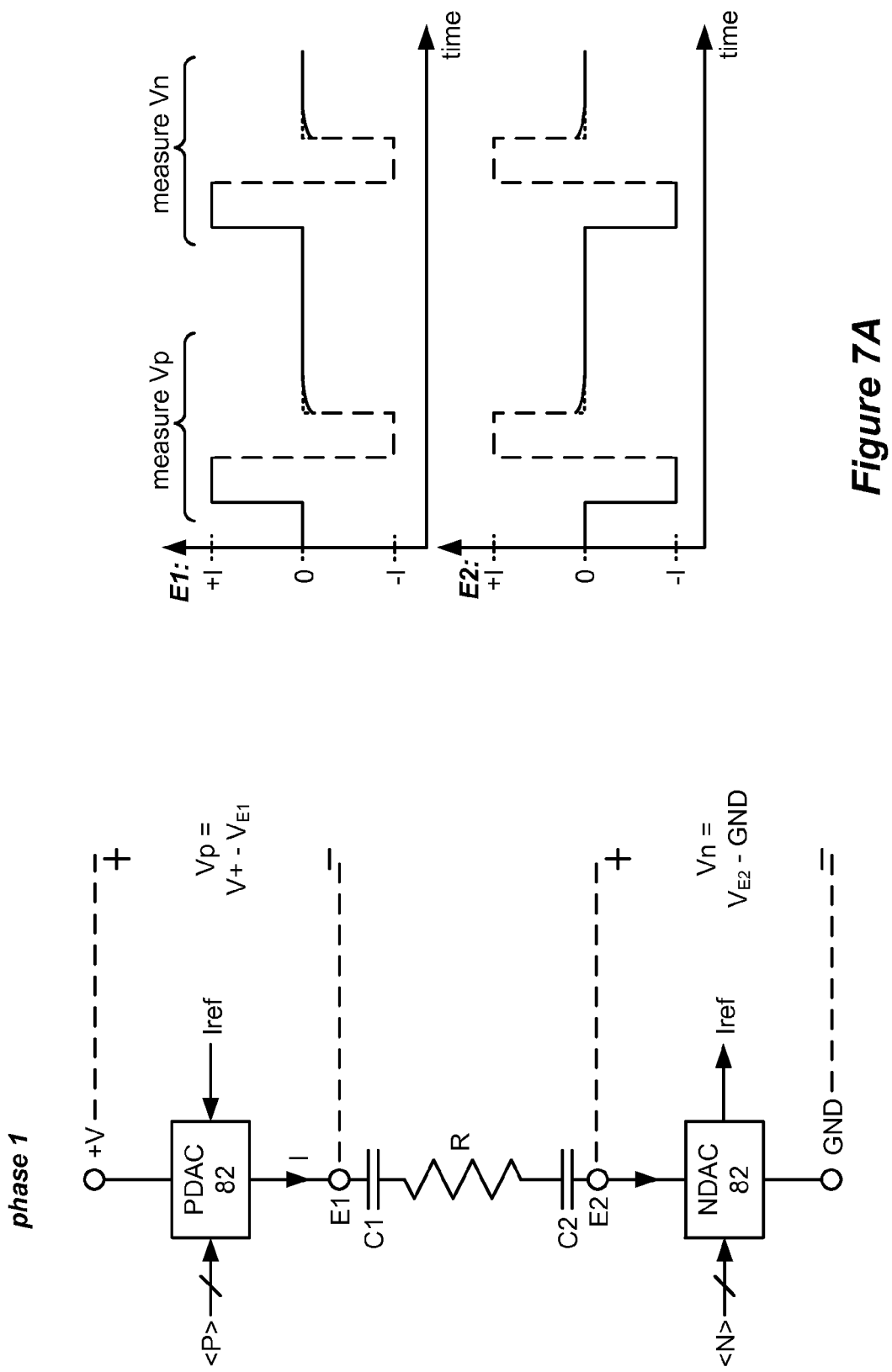
Figure 8A:
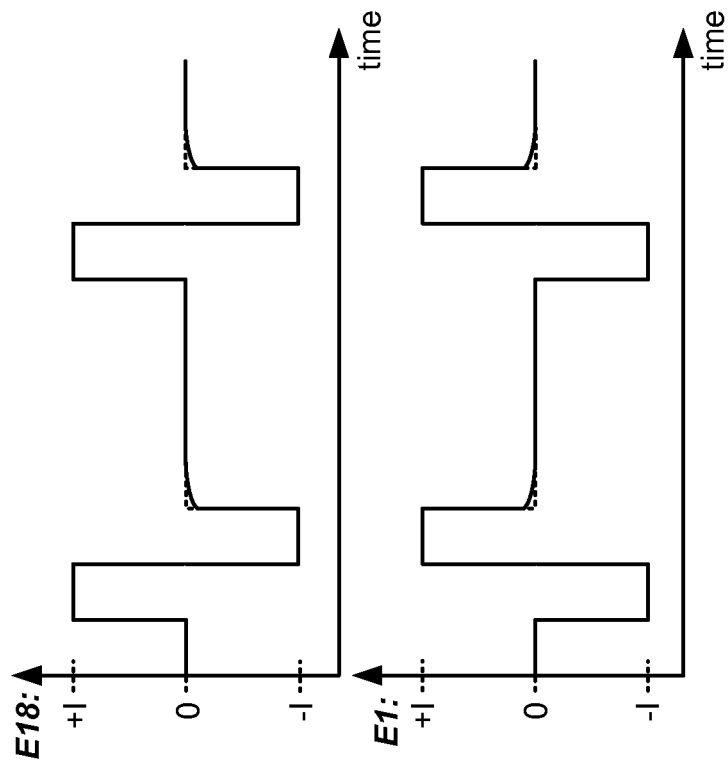
Figure 8A:
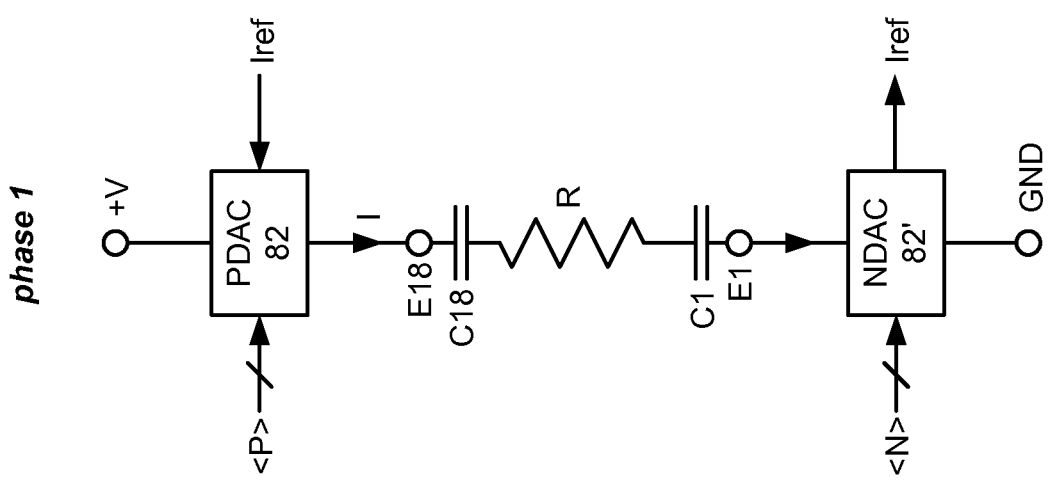

FIG. 7A illustrates voltage drops Vp and Vn across the PDAC and NDAC, once again using the example of a pulse between electrodes E1 and E2. Because this example is directed to optimizing the compliance voltage V+, it would be expected that the pulse comprises an actual therapeutic stimulation pulse instead of a test pulse. However, this is not strictly necessary, as it may be useful to also test the IPG and/or the compliance voltage generator 320 using the disclosed technique. The voltage drop across the PDAC 82 comprises the compliance voltage minus the voltage appearing at the anode electrode, i.e., Vp=V+$-V_{E1}$, while the voltage drop across the NDAC 82 comprises the voltage appearing at the cathode electrode minus ground, i.e., Vn=$V_{E2}$−0, or $V_{E2}$.

In this example, Vp is measured during provision of a first pulse in a pulse train, while Vn is measured during provision of a second (or later) pulse in the train. As will be seen shortly, and assuming that a biphasic pulse is used, these measurements are only taken during one phase of a biphasic pulse, which as illustrated is the first phase. Therefore, the second (or other) phase of the pulse is ignored and not used in the measurement, and thus it is shown in dotted lines in FIG. 7A. If a monophasic pulses are used, the measurement (not shown for simplicity) would be taken during the single phase of the pulse.

In the example illustrated, Vp is measured first, starting with FIG. 7B. FIG. 7B shows stage 1 of the measurement, i.e., the measurement as taken during the provision of the first phase of the biphasic pulse (or the only phase of a monophasic pulse). However, a pre-stage discharging of capacitors CX and CY occurs as shown in FIG. 6A, as does a blanking period. A figure is not included to once again illustrate the pre-stage capacitor discharge. Vp comprises the difference between V+ and E1, and so those inputs are selected by MUX1 and MUX2 respectively, thereby impressing their voltage difference on capacitor CX, i.e., $V_X$=V+$-V_{E1}$. As in the earlier resistance measurement, switches Sa and Sc are closed in stage 1, while switches Sb, Sd, and Se remain open. Note that due to the circuit structure, any parasitic voltage appearing at off-chip decoupling capacitor C1 is not included in the measurement.

If a biphasic pulse is used, stage 2 is simply bypassed, such that capacitor CY is simply not charged and retains its value of $V_Y$=0 as set pre-stage. Bypassing stage 2 can occur similarly to blanking, i.e., by opening all of switches Sa-Se during stage 2.

Next, during stage 3 (not illustrated), the capacitors CX and CY are connected in series, thus adding $V_X$ and $V_Y$ across the series connection, and the common mode inputs to the MUXes are chosen to set the common node between the capacitors to V+/2. This provides a voltage of V++½$V_{E1}$ to the input of buffer 311a and a voltage of ½$V_{E1}$ to the input of buffer 311b. This occurs as in FIG. 6D, and is not again included for simplicity. Referring the FIG. 7C, the buffers 311a and 311b are enabled, as is the differential amplifier 314, to output the difference V+$-V_{E1}$ to the A/D block 74, where it is digitized and stored.

FIGS. 7D and 7E show the measurement of Vn, which again is taken on a next (or later) pulse in the train. Again, pre-stage discharging of capacitors Cx and Cy are not shown. In FIG. 7D, during stage 1, MUX1 selects the cathode electrode E2, and MUX2 selects ground, thus impressing their difference, $V_{E2}$, on capacitor CX. Stage 2 is again by passed, and then the common mode inputs are chosen during stage 3 (not shown) to serially connect the capacitor, thus presenting ½(V++$V_{E2}$) and ½(V+$-V_{E2}$) to the input of buffers 311a and 311b respectively. When the buffers 311a and 311b and differential amplifier 314 are enabled as shown in FIG. 7E, the difference, $V_{E2}$ is outputted, digitized, and stored as was Vp previously. Again, notice that the parasitic voltage across decoupling capacitor $V_{C2}$ does not play into the Vn measurement.

As with the resistance measurement of FIGS. 6A-6E, the Vp and Vn measurements can be repeated and averaged to improved their accuracy. Once determined, Vp and Vn can then be used by the microcontroller 305 and the V+ generator 320 to set the compliance voltage V+ to an optimal level, using for example the technique disclosed in U.S. Pat. No. 7,444,181. As this optimal value for V+ would be expected to change over time due to the uncertain and perhaps changing nature of the patient's tissue, it is preferable to monitor Vp and Vn from time to time, and to adjust V+ on the fly during therapeutic stimulation.

FIGS. 8A-8F once again illustrate use of the sample and hold circuitry 310 to measurement resistance, but in an application having a master IC 300 and a slave IC 300' daisy chained together. In the example shown in FIG. 8A, resistance is measured between two electrodes appearing on different of the ICs 300 and 300': anode electrode E18 appears on the slave IC 300' and cathode electrode E1 appears on the master IC 300. Note that measuring resistance between two electrodes in a system having daisy-chained ICs 300 and 300' is discussed in the above-incorporated concurrent application. Because how this occurs is discussed in detail in that concurrently application, and is assumed familiar to the reader, the present disclosure limits discussion of the technique to the particular sample and hold circuit 310 that is the focus of this disclosure.

When one of the voltages being measured comes from the slave IC 300' instead of the master 300, the interconnection between the two sample and hold circuitries 310 and 310' is implicated, as shown in FIG. 8B. (Because the master and slave ICs 300 and 300' are identical, the same components are denoted either without a prime symbol in the master IC 300, and with a prime symbol in the slave IC 300'). Interconnection involves the use of off-bus signals IN1, IN2, OUT1, and OUT2. OUT1 from MUX1 on the slave IC 300' is sent to IN1 in the master IC 300, which in turn is sent as an input to both of the master IC's MUXes. OUT2 from MUX2 on the slave IC 300' is sent to IN2 in the master IC 300, which again is sent as an input to both of the master IC's MUXes. This interconnection of the sample and hold circuitries 310 and 310' operates to pull any relevant voltages to be monitored (e.g., $V_{E18}$) from the sample and hold circuitry 310' in the slave IC 300' to the sample and hold circuitry 310 in the master IC 300. Because the holding circuitry 314' is not used in the slave IC 300', it is illustrated in dotted lines in the Figures. This interconnection of the sample and hold circuitries 310 and 310' also results in inputs IN1 and IN2 to the MUXes in the slave IC 300' not being used, and the outputs OUT1 and OUT2 in the master IC 300 not being used, which again is represented by dotted lines. Routing on the PCB between the two IC 300 and 300' establishes the proper connections between OUT1 and OUT2 from the slave IC 300', and IN1 and IN2 in the master IC 300.

FIG. 8B shows configuration of the sample and hold circuitry 310 pre-stage, and is similar to FIG. 6A discussed earlier. Both MUXes in the master sample and hold 310 choose the ground input, and all of switches Sa-Se are closed, which shorts the capacitors CX and CY.

After a blanking period, FIG. 8C shows measurement of the electrode voltages E18 and E1 during stage 1. Because E18 acts as the anode during this phase, and thus would be biased to a higher voltage, it is selected by the top MUX1. However, this voltage must first be pulled from the slave IC 300' to the master IC. To do this, MUX1' in the slave selects the E2 input—the input corresponding to electrode E18. Switch S1' is closed to pass this selection to OUT1, which appears at inputs IN1 in the MUXes in the master IC 300. MUX1 in the sample and hold circuit 310 in the master selects this input IN1, thus impressing the voltage at E18 on the top of capacitor CX. Because E1 acts as the cathode, and thus would be biased to a lower voltage, it is selected by bottom MUX2, and because this electrode is already present at the master IC 300, it doesn't need to be pulled from the slave. Selecting E1 impresses the voltage at E1 on the bottom of capacitor CX. When parasitic voltages from the electrodes' decoupling capacitors are included, the voltage stored at capacitor CX, $V_X$, equals $V_{C18}+IR+V_{C1}$.

After another blanking period, FIG. 8D shows measurement of the electrode voltages during stage 2. Because E1 acts as the anode during this phase, and thus would be biased to a higher voltage, it is selected by the top MUX1. Because E18 acts as the cathode, and thus would be biased to a lower voltage, it is ultimately selected by bottom MUX2, but must first be pulled from the slave IC 300'. Here, MUX2' at the slave selects E18 (the E2 input), and switch S2' is closed to pass this selection to OUT2. This output is selected at MUX2 in the master as input IN2. This impress $V_Y=-V_{C1}+IR-V_{C18}$ across capacitor CY.

FIGS. 8E and 8F are essentially the same as FIGS. 6D and 6E earlier, and illustrate the stage 3 and post-stage portions of the resistance measurement. By way of review, during stage 3 (FIG. 8E), capacitors CX and CY are connected in series and their common node is biased to V+/2. The effect is to present a voltage of (V+/2)+IR to the top buffer 311a, and a voltage of (V+/2)−IR to the bottom buffer 311b. In the post-stage (FIG. 8F), the output buffers 311a and 311b are enabled to pass their voltages to the inputs of the differential amplifier 312, which is also enabled. The result at output 315 is an analog signal of 2IR, which output 315 is thereafter sent to the A/D block 74 (FIG. 3B), where it is digitized and stored. From there, the microcontroller 305 can read the digitized value by addressing the value as stored at the A/D block 74, and can process it to determine the resistance between electrode E1 and E2, for example, by dividing the digitized value by 2I. The microcontroller 305 may also subtract any AC offset voltage caused by AC charging of the decoupling capacitors C18 and C1 during the measurement, as discussed earlier.

Although not illustrated, it should be understood that the daisy-chained sample and hold circuitries 310 and 310' can also be used to monitor more than one voltage from the slave IC 300'. For example, if it was necessary to measure the resistance between two electrodes both appearing on the slave IC 300' (e.g., electrodes E23 and E24), both of these electrodes voltages would be pulled to the master IC 300, which would entail simultaneously using both of the MUXes in the slave to select these voltages, closing of both switches S1' and S2', and selection of both of the outputs OUT1 and OUT2 at inputs IN1 and IN2 at the MUXes on the master IC 300.

Although particular embodiments of the present invention have been shown and described, it should be understood that the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. Circuitry for an implantable stimulator device configured to provide a stimulation pulse having at least first and second phases between first and second electrodes, the circuitry comprising:
   a first capacitor;
   a second capacitor; and
   switching circuitry, wherein the switching circuitry is configured to:
      store a first voltage between the first and second electrodes across the first capacitor during the first pulse phase,
      store a second voltage between the first and second electrodes across the second capacitor during the second pulse phase, and
      serially connect the first and second capacitors to produce a sum of the first and second voltage after the second pulse phase.

2. The circuitry of claim 1, further comprising:
   a first multiplexer; and
   a second multiplexer,
   wherein the first multiplexer is configured to select a voltage of the first electrode during the first pulse phase, and wherein the second multiplexer is configured to select a voltage of the second electrode during the first pulse phase, to store the first voltage, and
   wherein the first multiplexer is configured to select the voltage of the second electrode during the second pulse phase, and wherein the second multiplexer is configured to select the voltage of the first electrode during the second pulse phase, to store the second voltage.

3. The circuitry of claim 1, wherein the first and second pulse phases are of opposite polarity.

4. The circuitry of claim 1, further comprising a differential amplifier, wherein the summed voltage is provided to the differential amplifier by providing a voltage at a first end of the serial connection to a first input of the differential amplifier and by providing a voltage at a second end of the serial connection to a second input of the differential amplifier.

5. The circuitry of claim 4, wherein the first input of the differential amplifier is provided via a first buffer, and wherein the second input of the differential amplifier is provided via a second buffer.

6. The circuitry of claim 1, further comprising logic circuitry configured to determine a resistance between the first and second electrodes using the summed voltage.

7. The circuitry of claim 6, wherein the stimulation pulse has a current of +I and −I during the first and second pulse phases respectively, and wherein the logic circuitry determines the resistance by dividing the summed voltage by 2I.

8. Circuitry, comprising:
   a first multiplexer configured to select from a plurality of first inputs to provide a first output;
   a second multiplexer configured to select from a plurality of second inputs to provide a second output;
   a first capacitor having a first plate and a second plate;
   a second capacitor having a first plate and a second plate;
   a first switch for coupling the first output to the first plate of the first capacitor;
   a second switch for coupling the first output to the first plate of the second capacitor;
   a third switch for coupling the second output to the second plate of the first capacitor;
   a fourth switch for coupling the second output to the second plate of the second capacitor; and
   a fifth switch for coupling the second plate of the first capacitor to the first plate of the second capacitor.

9. The circuitry of claim 8, wherein the plurality of first inputs and the plurality of second inputs each comprise voltages at a plurality of electrode nodes in an implantable stimulator.

10. The circuitry of claim 9, wherein the plurality of first inputs and the plurality of second inputs each further comprise at least one DC voltage.

11. The circuitry of claim 10, wherein the at least one DC voltage is selected from the group consisting of one or more of a ground, a voltage of a battery in the implantable stimulator, and a compliance voltage for powering stimulation circuitry in the implantable stimulator.

12. The circuitry of claim 11, wherein the plurality of first inputs and the plurality of second inputs each further comprise a common mode input.

13. The circuitry of claim 8, wherein the first and second capacitors are of equal capacitance.

14. The circuitry of claim 8, further comprising a differential amplifier for receiving a first voltage at a first plate of first capacitor and for receiving a second voltage at a second plate of the second capacitor, wherein the differential amplifier is configured to output an analog voltage comprising a difference between the first and second voltages.

15. The circuit of claim 14, further comprising an analog-to-digital converter for digitizing the analog voltage.

16. A method for measuring the resistance between first and second electrodes in an implantable stimulator device, comprising:
   (a) providing a first pulse of a first polarity to a first electrode and of a second polarity to a second electrode;
   (b) storing a first voltage between the first and second electrodes across a first capacitor during the first pulse;
   (c) providing a second pulse of the second polarity to the first electrode and of the first polarity to a second electrode;
   (d) storing a second voltage between the first and second electrodes across a second capacitor during the second pulse;
   (e) serially connecting the first and second capacitors to produce a sum of the first and second voltage after the second pulse; and
   (f) assessing the summed voltage to determine the resistance between the first and second electrode.

17. The method of claim 16, wherein the first and second pulses have a current magnitude of I.

18. The method of claim 16, wherein the first and second pulses are of the same duration.

19. The method of claim 16, further comprising during step (e) coupling a node between the serially-connected first and second capacitors to a common mode voltage.

20. The method of claim 19, wherein the first and second pulses are provided using a compliance voltage, and wherein the common mode voltage comprise one-half the compliance voltage.

21. The method of claim 16, wherein step (f) comprises use of a differential amplifier for presenting at an analog output the summed voltage.

22. The method of claim 17, wherein the resistance is determined in step (f) by logic circuitry that divides the summed voltage by 2I.

* * * * *